United States Patent [19]
Liu et al.

[11] Patent Number: 6,156,308
[45] Date of Patent: *Dec. 5, 2000

[54] *BACILLUS THURINGIENSIS* STRAINS ACTIVE AGAINST LEPIDOPTERAN AND COLEOPTERAN PESTS

[75] Inventors: Chi-Li Liu; Lee Fremont Adams; Patricia A. Lufburrow; Michael David Thomas, all of Davis, Calif.

[73] Assignee: Valent BioSciences, Inc., Libertyville, Ill.

[ * ] Notice: This patent is subject to a terminal disclaimer.

[21] Appl. No.: 09/032,869

[22] Filed: Mar. 2, 1998

Related U.S. Application Data

[60] Continuation of application No. 08/530,845, May 3, 1995, abandoned, which is a division of application No. 08/337,358, Nov. 10, 1994, Pat. No. 5,879,676, which is a continuation-in-part of application No. 08/264,100, Jun. 22, 1994, abandoned, which is a continuation-in-part of application No. 08/194,651, Feb. 9, 1994, abandoned, which is a continuation-in-part of application No. 08/166,391, Dec. 13, 1993, abandoned, which is a continuation-in-part of application No. 07/991,073, Dec. 15, 1992, abandoned.

[51] Int. Cl.$^7$ .............................. A01N 63/02; C12N 1/20; C12N 1/21; C12N 15/32

[52] U.S. Cl. ..................... 424/93.461; 424/93.2; 530/350; 536/23.71; 435/252.31; 435/252.5; 435/71.3; 514/12

[58] Field of Search .............................. 424/93.461, 93.2; 514/12; 530/350; 536/23.71; 435/252.31, 252.5, 71.3

[56] References Cited

U.S. PATENT DOCUMENTS

| | | | |
|---|---|---|---|
| 4,910,016 | 3/1990 | Gaertner et al. | 424/93 |
| 5,024,837 | 6/1991 | Donavan et al. | 424/93 |
| 5,039,523 | 8/1991 | Payne et al. | 424/93 |
| 5,073,632 | 12/1991 | Donovan | 536/27 |
| 5,126,133 | 6/1992 | Payne et al. | 424/93 |
| 5,135,867 | 8/1992 | Payne et al. | 435/252.33 |

FOREIGN PATENT DOCUMENTS

| | | |
|---|---|---|
| 9013651 | 11/1990 | WIPO . |
| 9304587 | 3/1993 | WIPO . |

OTHER PUBLICATIONS

Blenk, et al., *Chem. Abstracts*, vol. 115, Ab. #87508m (1991).

Chestukhina, et al., *FEBS Lett.*, vol. 232, pp. 249–251 (1988).

Hofte et al., *Micro. Review*, vol. 53, No. 2, pp. 242–255 (1989).

Tailor, et al., *Molecular Biology*, vol. 6, pp. 1211–1217 (1992).

*Primary Examiner*—Rebecca E. Prouty
*Attorney, Agent, or Firm*—Rockey, Milnamow & Katz, Ltd

[57] ABSTRACT

The invention is related to a novel biologically pure *Bacillus thuringiensis* (*B.t.*) strains active against lepidopteran and coleopteran pests which produces a bipyramidal crystal consisting essentially of at least two delta-endotoxins having a molecular weight of about 130,000 daltons and a rhomboidal crystal consisting essentially of two delta-endotoxins, each having a molecular weight of about 33,000 daltons, as well as spores, crystals, delta-endotoxins and/or mutants thereof. The invention also relates to insecticidal compositions obtainable therefrom. The invention further relates to methods of using the insecticidal compositions to control an insect pest(s) from the order Lepidoptera and/or Coleoptera. The invention also relates to isolated DNA sequences encoding the delta-endotoxins.

2 Claims, 4 Drawing Sheets

Figure 3A. Homology of the "MIVDL" protein to the 34 kdal protein of *B. thuringiensis* subsp. *thompsoni* and CryIAa of *B. thuringiensis* subsp. *kurstaki*.

MIVDL (1-294)
Thompsoni 34 kdal protein

| | | | | | | |
|---|---|---|---|---|---|---|
| Initial Score | = | 33 | Optimized Score | = | 119 | Significance = 6.06 |
| Residue Identity | = | 21% | Matches | = | 61 | Mismatches = 199 |
| Gaps | = | 30 | Conservative Substitutions | | | = 0 |

```
            10        20        30        40        50        60
    MIVDLYRYLGGLAAVNAVLHFYEPRPDICRNISEEYNLI---VFGDRIPTFSIDPSQININNLSVDTPVDEI
             ||          |                          | | |
        MAIMN---DIAQDAARAWDIIAGPFIRPGTTPTNRQLFNYQIGNIEVE--PGNL
        X         10        20        30        40

70        80        90       100       110       120       130
    TINNVRSIQLISS--RFENTGFVDTENYFTPELSRTVVNSISTSTTTGYKYTQSLTVSSKFSFNFPVAGAEN
    |       |  ||     |||      ||  | | |          | ||         |       |
    NFSVVPELDFSVSQDLFNNTSVQQSQT-ASFNESRT--ETTSTAVTHGVKSGVTVSASAKFNAKILVKSIEQ
    50        60        70        80        90       100       110

140       150       160       170       180       190       200
    NISFSVGFEQNLSTTETKTESTSTLMRIPPQPVSVRP--RTAKRVEISLFELAIPRIQNEISGFV---TGTL
    |  |  | | | | | |     |  | | | | |     |         |     |     |   ||||
    TITTTVSTEYNFSSTTTRTNTVTRGWSI-AQPVLVPPHSRVTATLQIYKGDFTVPVL---LSLRVYGQTGTL
    120       130       140       150       160       170       180

210       220       230       240       250       260       270
    PTISNSHISDLYAVLTRTDSL--CPNSYINRDDFLRIDHENRGLGLQGF--GSLTGNLTSLDFAIRTTEYDL
    |   |  |||  |        |              |            | |          |
    -AGNPSFPS-LYA-ATYENTLLGRIREHIAPPALFRASNAYISNGVQAIWRGTATTRVSQGLYSVVRIDERP
       190       200       210       220       230       240       250

280       290    X
    PSNTIINIENEIKRAHILTQ
                       |
    LAGYSGETRT-YYLPVTLSNSSQILTPGSLGSEIPIINPV
       260       270    X    280       290
```

Figure 3ẞ

MIVDL (1-294)
CryIAa

| | | | | | |
|---|---|---|---|---|---|
| Initial Score | = 12 | Optimized Score | = 119 | Significance | = 6.06 |
| Residue Identity | = 17% | Matches | = 57 | Mismatches | = 220 |
| Gaps | = 41 | Conservative Substitutions | | | = 0 |

```
                     X         10        20        30        40        50
                     MIVDL--YRYLGGLAAVNAVLHFYEPRPDICRNISEEYNLIVFGDRIPTFSI
                          ||     |       |      |                    ||
     WVRYNQFRRELTLTVLDIVALFSNYDSRRYP--IRTVSQLTREIYTNPVL-ENF--DGSFRGMAQRIEQNIR
       230       240    X 250       260       270       280       290

60        70        80        90       100       110
      DPSQINI-NNLSVDTPV----DEITINNVRSIQLISS--RFENTGFVDTENYFTPEL-SRTVVNSISTSTTT
       |  | |    | |                         |    |     |    |  |||   |
      QPHLMDILNSITIYTDVHRGFNYWSGHQITASPVGFSGPEFAFPLFGNAGNAAPPVLVSLTGLGIFRTLSSP
       300       310       320       330       340       350       360

120       130       140       150       160       170       180
      GYKYTQSLTVSSKFSFN--FPVAGAENNISFSVGFEQNLSTTETKTESTSTLMRIPPQPVSVRPRTAKRVEI
       |          |       |   |    ||       ||           |   ||||  || ||
      LYR---RIILGSGPNNQELFVLDGTE--FSFASLTTNLPSTIYRQRGTVDSLDVIPPQDNSVPPRAG----F
        370       380       390       400       410       420

190       200       210       220       230       240       250
      SLFELAIPRIQNEISGFV-TGTLPTISNSHIS-DLYAVLTRTDSLCPNSYINR-DDFLRIDHENRGLGLQGF
       |  |             |||      || |  |                              | | |
      S-HRLSHVTMLSQAAGAVYTLRAPTFSWQHRSAEFNNIIPSSQ--ITQIPLTKSTNLGSGTSVVKGPGFTGG
        430       440       450       460       470       480       490

260       270       280       290   X
          GSL----TGNLTSLDFAIRTTEYD-----LPSNTIINIENEIKRAHILTQ
           |      |    |  |    |
          DILRRTSPGQISTLRVNITAPLSQRYRVRIRYASTTNLQFHTSIDGRPINQGNFSATMSSGSNLQSGSFR
            500       510       520       530       540    X 550       560
```

BACILLUS THURINGIENSIS STRAINS ACTIVE AGAINST LEPIDOPTERAN AND COLEOPTERAN PESTS

This is a continuation of U.S. patent application Ser. No. 08/530,845 filed May 3, 1995 now abandoned, which is a divisional of U.S. patent application Ser. No. 08/331,358, filed Nov. 10, 1994, now U.S. Pat. No. 5,879,676, which is a continuation-in-part of application Ser. No. 08/264,100, filed Jun. 22, 1994, now abandoned, which is a continuation-in-part of Ser. No. 08/194,651, filed Feb. 9, 1994, now abandoned, which is a continuation-in-part of application Ser. No. 08/166,391, filed Dec. 13, 1993, now abandoned which is a continuation-in-part of application Ser. No. 07/991,073, filed Dec. 15, 1992, now abandoned.

1. FIELD OF THE INVENTION

The invention is related to a novel biologically pure *Bacillus thuringiensis* (*B.t.*) strain(s) active against lepidopteran and coleopteran pests which produces a bipyramidal crystal consisting essentially of at least two delta-endotoxins having a molecular weight of about 130,000 daltons and a rhomboidal crystal consisting essentially of two delta-endotoxins, each having a molecular weight of about 33,000 daltons, as well as spores, crystals, delta-endotoxins and/or mutants thereof. The invention also relates to insecticidal compositions obtainable therefrom. The invention further relates to methods of using the insecticidal compositions to control an insect pest(s) from the order Lepidoptera and/or Coleoptera. The invention also relates to isolated DNA sequences encoding the delta-endotoxins.

2. BACKGROUND OF THE INVENTION

Every year, significant portions of the world's commercially important agricultural crops, including foods, textiles, and various domestic plants are lost to pest infestation, resulting in losses in the millions of dollars. Various strategies have been used in attempting to control such pests.

One strategy is the use of broad spectrum pesticides, chemical pesticides with a broad range of activity. However, there are a number of disadvantages to using such chemical pesticides. Specifically, because of their broad spectrum of activity, these pesticides may destroy non-target organisms such as beneficial insects and parasites of destructive pests. Additionally, these chemical pesticides are frequently toxic to animals and humans, and targeted pests frequently develop resistance when repeatedly exposed to such substances.

Another strategy has involved the use of biopesticides, which make use of naturally occurring pathogens to control insect, fungal and weed infestations of crops. Biopesticides are naturally occuring organisms that produce a toxin(s), a substance toxic to the infesting agent which is generally less harmful to non-target organisms and the environment as a whole than chemical pesticides.

The most widely used biopesticide is *Bacillus thuringiensis* (*B.t.*). *B.t.* is a widely distributed, rod shaped, aerobic and spore forming microorganism. During its sporulation cycle, *B.t.* produces a protein(s) known as a delta-endotoxin(s), that forms crystalline inclusion bodies within the cell. The delta-endotoxins have molecular weights ranging from 27–140 kD and kill insect larvae upon ingestion.

Delta-endotoxins have been produced by recombinant DNA methods (see, for example, Tailor et al., 1992, Molecular Microbiology 6:1211–1217; toxin is active against lepidopteran and coleopteran pests; Payne et al., U.S. Pat. No. 5,045,469; toxin is active against lepidopteran pests). The delta-endotoxins produced by recombinant DNA methods may or way not be in crystal form.

A number of *B.t.* strains have been isolated that have been found to be active against insect pests of the order Lepidoptera. *B.t.* subsp. *kurstaki* HD-1 produces bipyramidal and cuboidal crystal proteins in each cell during sporulation (Lüthy et al., in Microbial and Viral Pesticides, ed. E. Kurstak, Marcel Dekker, New York, 1982, pp. 35–74); the bipyramidal crystal was found to be encoded by three cryIA genes (Aronson et al., 1986, Microbiol. Rev. 50:1–50). *B.t.* subsp. *kurstaki* HD-73 crystal delta-endotoxin contains the CryIA (c) protein (Adang et al., 1985, Gene 36:289–300). *B.t.* subsp. *dendrolimus* HD-7 and HD-37 contain a CryIA and a CryII protein; *B.t.* subsp. *sotto* contains an alkaline soluble protein that differs from the holotype CryIA(a) protein by 24 amino acids; *B.t.* subsp. *subtoxicus* HD-10 contains CryIA and CryIB proteins; *B.t.* subsp. *tolworthi* HD-121 contains CryIA and CryII proteins; and *B.t.* subsp. *aizawai* HD-68 contains CryIA proteins (Höfte and Whiteley, 1989, Microbiol. Reviews 53:242–255). Payne, U.S. Pat. No. 4,990,332, issued Feb. 5, 1993, discloses an isolate of *B.t.*, PS85AI, and a mutant of the isolate, PS85AI, which both have activity against *Plutella xylostella*, a lepidopteran pest, and produce alkaline soluble proteins having a molecular weight of 130,000 and 60,000 daltons. Payne, U.S. Pat. No. 5,045,469, issued Sep. 3, 1991 discloses a *B.t.* isolate designated PS81F which also produces alkaline soluble proteins having a molecular weight of 130,000 and 60,000 daltons and has activity against *Spodoptera exigua* and *T. ni*; the toxin gene from PS81F appears to have little homology to the toxin gene from *B.t.* subsp. *kurstaki* HD-1. Payne, U.S. Pat. No. 5,206,166, filed Jun. 25, 1992, issued Apr. 27, 1993, discloses *B.t.* isolates PS81A2 and PS81RR1 which produce 133,601 and 133,367 dalton alkaline-soluble proteins; both have activity against *Trichoplusia ni, Spodoptera exigua* and *Plutella xylostella* and are different from *B.t.* Subsp. *kurstaki* HD-1 and other *B.t.* isolates Bernier et al., U.S. Pat. No. 5,061,489 and WO 90/03434 discloses strain A20 producing a delta-endotoxin encoded by at least three genes: 6.6-, 5.3-, and 4.5-type genes (cryIA(a), cryIA(b), and cryIA(c)). Chestukhina et al., 1988, FEBS Lett. 232:249–51, disclose that *B.t.* subsp. *galleriae* produces two delta-endotoxins, both of which are active against lepidopteran pests.

Other strains, e.g. *Bacillus thuringiensis* subsp. *tenebrionis* (Krieg et al., 1988, U.S. Pat. No. 4,766,203), have been found to be specific for Coleoptera. The isolation of another coleopteran toxic *Bacillus thuringiensis* strain was reported in 1986 (Hernnstadt et al. Bio/Technology vol. 4, 305–308, 1986, U.S. Pat. No. 4,764,372, 1988). This strain, designated "*Bacillus thuringiensis* subsp. *san diego*", M-7, has been deposited at the Northern Regional Research Laboratory, USA under accession number NRRL B-15939. However, the assignee of the '372 patent, Mycogen, Corp. has publicly acknowledged that *Bacillus thuringiensis* subsp. *san diego* is *Bacillus thuringiensis* subsp. *tenebrionis*.

Other isolated strains have been found to be active against two orders of pests. Padua, 1990, Microbiol. Lett. 66:257–262, discloses the isolation of two mutants containing two delta-endotoxins, a 144 kD protein having activity against a lepidopteran pest and a 66 kD protein having activity against mosquitoes. Bradfish et al., U.S. Pat. No. 5,208,017, discloses *B.t.* isolates PS86A1 and PS86Q3 which produce alkaline soluble proteins having a molecular weight of 58,000 and 45,000 daltons and 155,000, 135,000, 98,000, 62,000, and 58,000 daltons, respectively and which have activity against lepidopteran and coleopteran pests. PCT Application No. WO 90/13651 and Tailor et al., 1992, Molecular Microbiology 6:1211–1217, disclose a B.t. strain which is toxic against Lepidoptera and Coleoptera and which produces a toxin having a molecular weight of 81 kd.

It is advantageous to isolate new strains of *Bacillus thuringiensis* to produce new toxins so that there exists a wider spectrum of biopesticides for any given insect pest.

3. SUMMARY OF THE INVENTION

The invention is related to a novel biologically pure *Bacillus thuringiensis* strain(s) or a spore(s), crystal(s) or mutant(s) thereof which strain or mutant in contrast to *B.t.* strains disclosed in the prior art, has activity against an insect pest of the order Lepidoptera and an insect pest of the order Coleoptera, produces at least two delta-endotoxins having a molecular weight of about 130,000 daltons and two delta-endotoxins both having molecular weights of about 33,000 daltons. One of the 33,000 dalton delta-endotoxins has an amino acid sequence essentially as depicted in SEQ ID NO:37 (hereinafter referred to as the "MIVDL protein"). The other 33,000 dalton delta-endotoxin has an amino acid sequence essentially as depicted in SEQ ID NO:38 (hereinafter referred to as the "MKHHK protein"). The 130,000 delta-endotoxins have insecticidal activity against insect pests of the order Lepidoptera.

The invention also relates to each of the delta-endotoxins as well as an isolated nucleic acid fragment containing a nucleic acid sequence encoding each of the delta-endotoxins or a portion of the delta-endotoxin having insecticidal activity against a pest. In one embodiment, the nucleic acid fragment contains a nucleic acid sequence encoding the MIVDL protein and may have the nucleic acid sequence essentially as depicted in SEQ ID NO:39. In another embodiment, the nucleic acid fragment contains a nucleic acid sequence encoding the MKHHK protein and may have the nucleic acid sequence essentially as depicted in SEQ ID NO:40. The invention is also directed to a genomic sequence comprising nucleic acid sequence encoding the MYHHK and/or MIVDL and may have the nucleic acid sequence essentially as depicted in SEQ ID NOS: 41 (MKHHK and MIVDL), 44 (MKHHK), and 45 (MIVDL)

The invention also provides vectors, DNA constructs and recombinant host cells comprising the claimed nucleic acid fragment(s), which vectors, DNA constructs and recombinant host cells are useful in the recombinant production of the delta-endotoxins of the present invention. The nucleic acid fragment may be operably linked to transcription and translation signals capable of directing expression of the delta-endotoxin in the host cell of choice. Recombinant production of the delta-endotoxin(s) of the invention is achieved by culturing a host cell transformed or transfected with the nucleic acid fragment of the invention, or progeny thereof, under conditions suitable for expression of the delta-endotoxin, and recovering the delta-endotoxin from the culture.

The invention is further related to an oligonucleotide probe having a nucleotide sequence essentially as depicted in SEQ ID NO:20 which can be used to detected the MIVDL protein and and oligonucleotide probe essentially as depicted in SEQ ID NO:21 which can be used to detect the MKHHK protein.

In a specific embodiment of the invention, the *thuringiensis* strain of the present invention is EMCC0075 and EMCC0076 having the identifying characteristics of NRRL B-21019 and NRRL B-21020 respectively.

The novel *Bacillus thuringiensis* strains, spores, mutants or crystals and/or delta-endotoxins may within the scope of this invention each be formulated into insecticidal compositions. In one embodiment, the strain, spores, mutants, crystals, and/or delta-endotoxins may be combined with an insecticidal carrier. Insecticidal compositions comprising the strains or mutants of the invention and/or spores, and/or crystals thereof may be used to control insect pests of the order Lepidoptera and and/or insect pests of the order Coleoptera in a method comprising exposing the pest co an insect-controlling effective amount of such an insecticidal composition.

Furthermore, the compositions or delta-endotoxins of the present invention may be used to enhance the insecticidal activity of another Bacillus-related insecticide. As defined herein, "a Bacillus related insecticide" is a Bacillus (e.g., *Bacillus thuringiensis*, specifically, *Bacillus thuringiensis* subsp. *kurstaki* or *Bacillus thuringiensis* subsp. *tenebrionis* or *Bacillus subtilis*) strain, spore, or substance, e.g., protein or fragment thereof having activity against or which kill insects; a substance that provides plant protection, e.g. antifeeding substance; or a microorganism capable of expressing a Bacillus gene encoding a Bacillus protein or fragment thereof having activity against or which kills insects (e.g., *Bacillus thuringiensis* delta-endotoxin) and an acceptable carrier (see Section 5.2., infra, for examples of such carriers). A microorganism capable of expressing a Bacillus gene encoding a Bacillus protein or fragment thereof having activity against or which kill insects inhabits the phylloplane (the surface of the plant leaves), and/or the rhizosphere (the soil surrounding plant roots), and/or aquatic environments, and is capable of successfully competing in the particular environment (crop and other insect habitats) with the wild-type microorganisms and provide for the stable maintenance and expression of a Bacillus gene encoding a Bacillus protein or fragment thereof having activity against or which kill insects. Examples of such microorganisms include but are not limited to bacteria, e.g., genera Bacillus, Pseudomonas, Erwinia, Serratia, Klebsiella, Xanthomonas, Streptomyces, Rhizobium, Rhodopseudomonas, Methylophilius, Agrobacterium, Acetobacter, Lactobacillus, Arthrobacter, Azotobacter, Leuconostoc, Alcaligenes, and Clostridium; algae, e.g. families Cyanophyceae, Prochlorophyceae, Rhodophyceae, Dinophyceae, Chrysophyceae, Prymnesiophyceae, Xanthophyceae, Raphidophyceae Bacillariophyceae, Eustigmatophyceae, Cryptophyceae, Euglenophyceae, Prasinophyceae, and Chlorophyceae; and fungi, particularly yeast, e.g., genera Saccharomyces, Cryptococcus, Kluyveromyces, Sporobolomyces, Rhodotorula, and Aureobasidium.

In a specific embodiment, the delta-endotoxins or compositions of the present invention may act together with Bacillus-related insecticides in a synergistic fashion. In another embodiment, Bacillus strains active against insect pests of the order Coleoptera may act together in a synergistic fashion with delta-endotoxins, Bacillus strains or spores thereof active against insect pests of the order Lepidoptera to kill insect pests of the order Coleoptera. In yet another embodiment, the delta-endotoxins of the present invention may act together in a synergistic fashion.

4. BRIEF DESCRIPTION OF THE FIGURES

FIG. 1 shows the results of PCR analysis of *Bacillus thuringiensis* strains for cryI genes by agarose gel electrophoresis. Lane 1 shows molecular weight markers (1 kb ladder, BRL-GIBCO). Lanes 2 and 3 show analysis of strains EMCC0075 and EMCC0076 with cryID oligonucleotide primers described in FIG. 1. Lanes 4–6 show the analysis of *Bacillus thuringiensis* subsp. *tenebrionis*, an unknown *Bacillus thuringiensis* strain, and *Bacillus thuringiensis* subsp. *aizawai* with cryID oligonucleotide primers. *Bacillus thuringiensis* subsp. *tenebrionis* contains only the cryIIIA gene; the unknown *Bacillus thuringiensis* strain does not contain the cryID gene; and *Bacillus thuringiensis* subsp. *aizawai* contains several cryI genes including cryID.

FIGS. 3A and 3B shows the homology of the "MIVDL" protein to the 34 kDa protein of *Bacillus thuringiensis* subsp. *thompsoni* and the CryIA(a) protien of *Bacillus thuringiensis* subsp. *kurstaki*.

5. DETAILED DESCRIPTION OF THE INVENTION

5.1. OBTAINING DELTA-ENDOTOXINS

Figure 1:
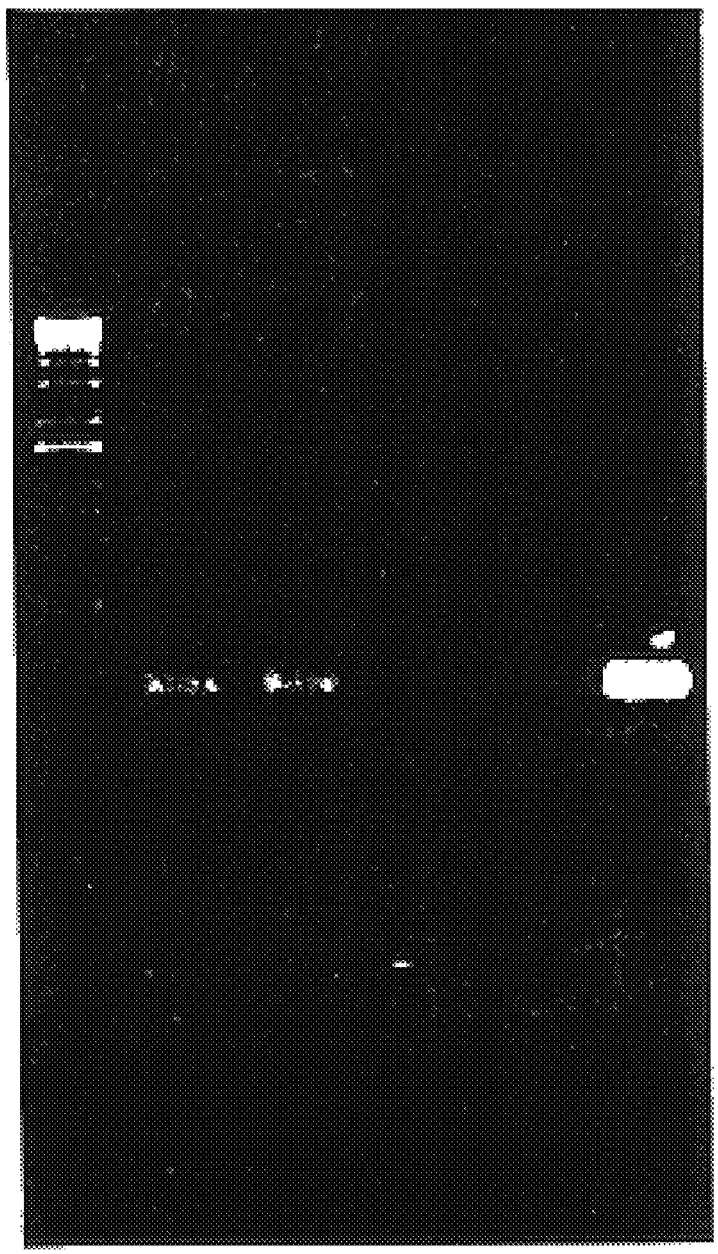

The spores and crystals of the present invention are obtainable from the strains of the present invention. The strains of the present invention may be cultured using media and fermentation techniques known in the art (see, for example, Rogoff et al., 1969, J. Invertebrate Path. 14:122–129; Dulmage et al., 1971, J. Invertebrate Path. 18:353–358; Dulmage et al., in Microbial Control of Pests and Plant Diseases, H. D. Burges, ed., Academic Press, N.Y., 1980). Upon completion of the fermentation cycle, the crystals and spores can be harvested by separating *B.t.* spores and crystals from the fermentation broth by means well known in the art, e.g. centrifugation. The spores and crystals are contained in the pellet.

As noted in Section 2, supra, crystals consist essentially of a delta-endotoxin(s). The strains of the present invention produce two types of crystals. One is a bipyramidal crystal consisting essentially of at least two 130,000 dalton delta-endotoxins. The other is a rhomboidal crystal consisting essentially of the two 33,000 dalton delta-endotoxins.

Purification of the crystals or delta-endotoxins can be carried out by various procedures known in the art, including, but not limited to, density gradient centrifugation, chromatography (e.g. ion exchange, affinity, hydrophobic and size exclusion), electrophoretic procedures, differential solubility, or any other standard technique for the purification of proteins.

The delta-endotoxins may also be obtained from a recombinant DNA expression system. Specifically, DNA encoding each toxin as, for example, essentiaily depicted in SEQ ID NOS: 39, 40, 44 and 45 is cloned into a suitable DNA expression vector. Alternatively one genomic DNA fragment comprising nucleic acid sequences encoding each delta endotoxin as, for example, essentially depicted in SEQ ID NO:41 may be cloned.

Identification of the specific DNA fragment encoding the delta-endotoxin may be accomplished in a number of ways, including, but not limited to, electrophoretic separation of the fragments (Southern, 44 1975, J. Mol. Biol. 98:503) in agarose, transfer of the separated DNA fragments to nitrocellulose, nylon, or other suitable support medium, and probing of the transferred fragments with a degenerate oligonucleotide probe(s) based on the amino acid sequence of the protein as determined by sequential Edman degradation. Alternatively, one may probe with a labeled gene fragment corresponding to the open reading frame of a protein with suspected high homology to the protein of interest. High homology to the gene of interest may be determined by alignment of a family of related proteins and identification of highly conserved regions in the encoding DNA segments (see, for example, Gribskov, K., and J. Devereux, eds., in Sequence Analysis Primer, Stockton Press, N.Y., 1991). An elegant and reliable method is to determine the amino acid sequences of at least two peptide fragments, generated by enzymatic or chemical means from the protein of interest, design degenerate oligonucleotides that will recognize the DNA encoding those regions, and then to apply polymerase chain reaction (PCR) techniques to amplify perfect or near-perfect copies of the intervening region of DNA. This PCR-generated segment of DNA can then be labeled and used as a highly specific probe for cloning the delta-endotoxin-encoding gene.

Once identified, the DNA fragment harboring the gene encoding the delta-endotoxin or a portion thereof may be cloned by ligation of a size-selected library of fragments expected to harbor the gene of interest into a suitable vector including, but not limited to, pBR322, pUC118, pACYC194, and pBCSK plasmids and their variants for transformation into *Escherichia coli*; or pUB110, pBD64, pBC16, pHP13, pE194, pC194 and their variants, for transformation into Bacillus spp. Bacteriophage vectors, such as lambda and its derivatives, may also be used for cloning of the gene(s) into *E. coli*.

Production of the delta-endotoxin or a portion thereof at commercially useful levels can be achieved by subcloning the encoding gene into plasmid vectors that permit stable expression and maintenance in a suitable host. Frequently, acceptable expression can be achieved using the native regulatory elements present on the DNA fragment encoding the delta-endotoxin. However, one might wish to add or alter transcriptional regulatory signals (promoters, initiation start sites, operators, activator regions, terminators) and translational regulatory signals (ribosomal binding sites, initiation codons) for enhanced or more regulated expression of the delta-endotoxin gene within the chosen host cell.

In addition to plasmids, delta-endotoxin genes and the appropriate regulatory elements may be introduced into one of the native plasmids of *Bacillus thuringiensis* and/or another chosen host, or into the chromosomal DNA, via "gene conversion" (e.g., Iglesias and Trautner, 1983, Mol Gen. Genet. 189:73–76; Duncan et al., 1978, Proc. Natl. Acad. Sci. U.S.A. 75:3664–3665) or homologous recombination (e.g., Ferrari et al., 1983, J. Bacteriol. 154:1513–1515) at sites of shared DNA homology between the vector and the host strain. An efficient "two-plasmid" system may be used for introduction of genes into Bacilli via homologous recombination (see, for example, PCT Patent WO91/09129). Transposons may also be used to introduce cry genes into the selected host strain. For example, in the Bacilli, transposons such as Tn917 and its derivatives may be used (Youngman et al., 1989, In Regulation of Prokaryotic Development, I. Smith, R. Slepecky, and P. Setlow, eds., American Society for Microbiology, Washington, D.C.).

Transfer of cloned delta-endotoxin genes into *Bacillus thuringiensis*, as well as into other organisms, may be achieved by a variety of techniques, including, but not limited to, protoplasting of cells (Chang and Cohen, 1979, Mol. Gen. Genet. 168: 111–115; Crawford et al., 1987, J. Bacteriol. 169: 5423–5428); electroporation (e.g., Schurter et al., 1989, Mol. Gen. Genet. 218: 177–181 and Macaluso et al., 1991, J. Bacteriol. 173: 1353–1356); particle bombardment (e.g., Shark et al., 1991, Appl. Environ. Microbiol. 57:480–485); silicon carbide fiber-mediated transformation of cells (Kaeppler et al., 1992, Theor. Appl. Genet. 84:560–566); conjugation (Gonzalez et al., 1982, Proc. Natl. Acad. Sci. U.S.A. 79:6951–6955); or transduction by bacteriophage (e.g., Lecadet et al., 1992, Appl. Environ. Microbiol. 58: 840–849). Transformed colonies may be detected by their ability to produce crystal delta-endotoxin, to bind antibody directed against that specific delta-endotoxin, or to kill susceptible pests, e.g., arthropods or nematodes, in bioassay.

Criteria for selection of a particular host for production include, but are not limited to, ease of introducing the gene into the host, availability of expression systems, and stable maintenance and expression of the gene encoding the delta-endotoxin. The host may be a microorganism, such as *Bacillus thuringiensis* itself, or an inhabitant of the phytosphere, e.g., the phylloplane (the surface of plants), and/or the rhizosphere (the soil surrounding plant roots), and/or aquatic environments, and should be capable of competing in the particular environment (crop and other insect habitats) with the wild-type microorganisms. Examples of such microorganisms include but are not limited to bacteria, e.g. genera Bacillus, Pseudomonas, Erwinia, Serratia, Klebsiella, Xanthomonas, Streptomyces, Rhizobium, Rhodopseudomonas, Methylophilius, Agrobacterium, Acetobacter, Lactobacillus, Arthrobacter, Azocobacter, Leuconcostoc, Alcaligenes, and Clostridium; algae, e.g. families Cyanophyceae, Prochlorophyceae, Rhodophyceae, Dinophyceae, Chrysophyceae, Prymnesiophyceae, Xanthophyceae, Raphidophyceae, Bacillariophyceae, Eustigmatophyceae, Cryptophyceae, Euglenophyceae, Prasinophyceae, and Chlorophyceae; and fungi, particularly yeast, e.g. genera Saccharomyces, Cryptococcus, Kluyveromyces, Sporobolomyces, Rhodotorula, and Aureobasidium.

The gene(s) encoding the delta-endotoxin(s) of the present invention or a portion thereof can also be inserted into an appropriate cloning vector for subsequent introduction into the genomes of suitable plants that are known to be infested with insects susceptible to the delta-endotoxin(s), or into specific baculoviruses which can in turn be directly used as insecticides.

Figure 2:
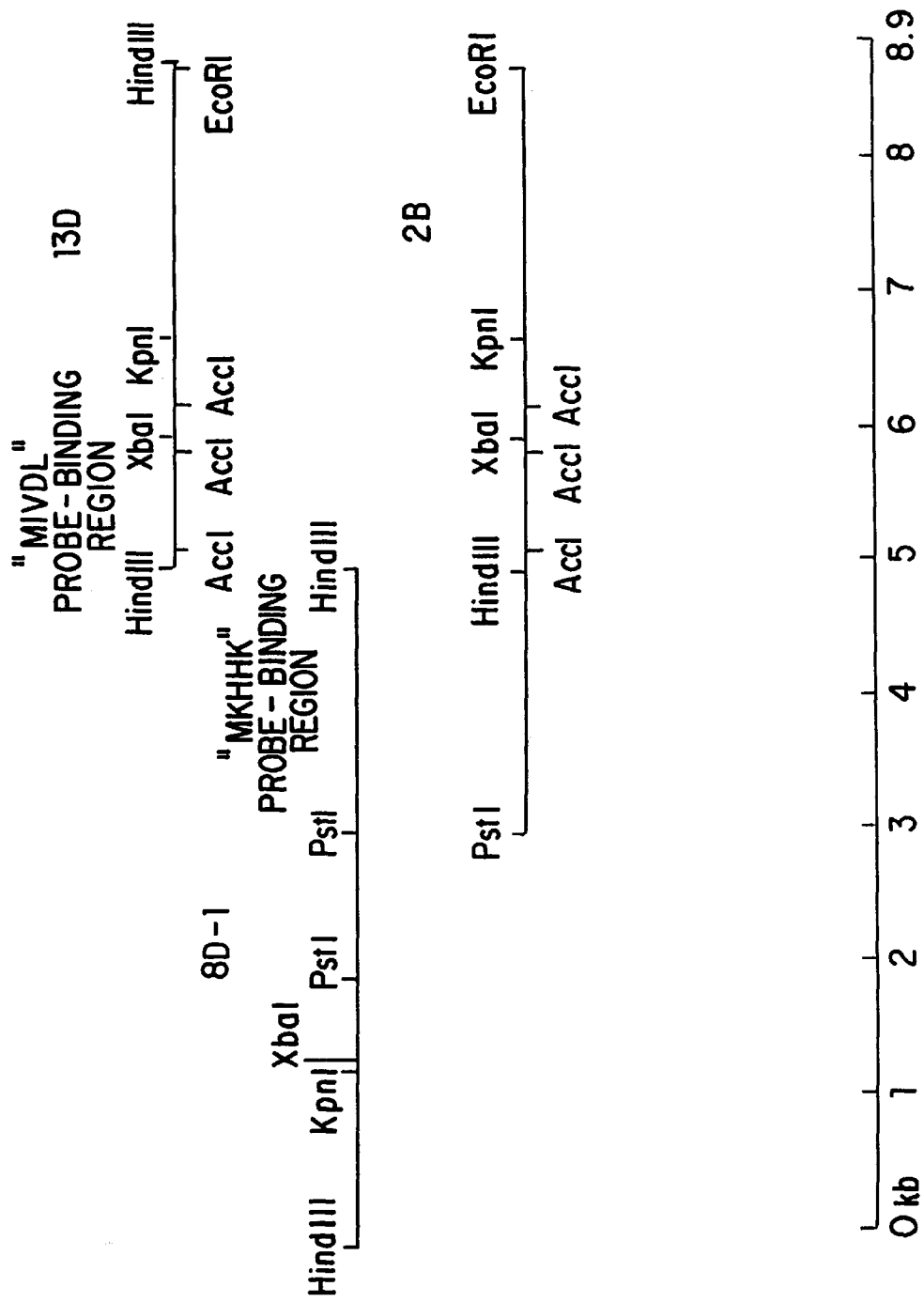
FIG. 2 shows the cloned DNA fragments which encode the MKHHK and MIVDL proteins.

Those skilled in the art will recognize that the invention is not limited to use of the nucleic acid fragments specifically disclosed herein, for example, in SEQ ID NO:39 OR 40. It will be apparent that the invention also encompasses those nucleotide sequences that encode the same amino acid sequences as depicted in SEQ ID NO:39 OR 40, but which differ from those specifically depicted nucleotide sequences by virtue of the degeneracy of the genetic code. The invention specifically encompasses any variant nucleotide sequence, and the protein encoded thereby, which protein retains at least about an 80%, preferably 90%, and most preferably 95% homology or identity with one or the other of the amino acid sequences depicted in FIG. 2 and retains the activity of the sequences described herein. In particular, variants which retain a high level (i.e., >80%) of homology at highly conserved regions of said delta-endotoxin are contemplated. Furthermore, the invention encompasses any variant thou hybridizes to the nucleotide sequence of the. delta-endotoxin under the following conditions: presoaking in 5× SSC and prehydbridizing for 1 hr at about 40° C. in a solution of 20% formamide, 5× Derhardt's solution, 50 mM sodium phosphate, pH 6.8, and 50 ug denatured sonicated calf thymus DNA, followed by hybridization in the same solution supplemented with 100 uM ATP for 18 hrs. at about 40° C., followed by a wash in 0.4× SSC at a temperature of about 45° C.

Useful variants within the categories defined above include, for example, ones in which conservative amino acid substitutions have been made, which substitutions do not significantly affect the activity of the protein. By conservative substitution is meant that amino acids of the same class may be substituted by any other of that class. For example, the nonpolar aliphatic residues Ala, Val, Leu, and Ile may be interchanged, as may be the basic residues Lys and Arg, or the acidic residues Asp and Glu. Similarly, Ser and Thr are conservative substitutions for each other, as are Asn and Gln. It will be apparent to the skilled artisan that such substitutions can be made outside the regions critical to the function of the molecule and still result in an active delta-endotoxin. Retention of the desired activity can readily be determined by using the assay procedures described below.

5.2. MUTANTS

The invention is also directed to a mutant *B.t.* strain which produces a larger amount of and/or larger crystals than the parental strain. A "parental strain" as defined herein is the original *Bacillus thuringiensis* strain before mutagenesis.

To obtain such mutants, the parental strain may, for example, be treated with a mutagen by chemical means such as N-methyl-N'-nitro-N-nitrosoguanidine or ethyl methanesulfonate, or by irradiation with gamma rays, X-rays or UV. Specifically, in one method of mutating *Bacillus thuringiensis* strains and selecting such mutants the following procedure is used:

i) the parental strain is treated with a mutagen;
ii) the thus presumptive mutants are grown in a medium suitable for the selection of a mutant strain; and
iii) the mutant strain is selected for increased production of delta-endotoxin.

According to a preferred embodiment of this method, the selected colonies are grown in a production medium, and a final selection for strains capable of increased delta-endotoxin production is performed.

Alternatively, the mutant(s) may be obtained using recombinant DNA methods known in the art. For example, a DNA sequence containing a gene coding for a delta-endotoxin may be inserted into an appropriate expression vector and subsequently introduced into the parental strain using procedures known in the art. Alternatively, a DNA sequence containing a gene coding for a delta-endotoxin may be inserted into an appropriate vector for recombination into the genome and subsequent amplification.

5.3. BIOASSAY

The activity of the *B.t.* strains of the present invention or spores, mutants, crystals, or delta-endotoxins thereof against various insect pests may be assayed using procedures known in the art, such as an artificial insect diet incorporation assay, artificial diet overlay; leaf painting, leaf dip, and foliar spray. Specific examples of such assays are given in Section 6, infra.

5.4. COMPOSITIONS

The strains, spores, crystals, delta-endoxins, or mutants of the present invention described supra can be formulated with an acceptable carrier into an insecticidal composition(s) that is, for example, a suspension, a solution, an emulsion, a dusting powder, a dispersible granule, a wettable powder, an emulsifiable concentrate, an aerosol or impregnated granule.

Such compositions disclosed above may be obtained by the addition of a surface active agent, an inert carrier, a preservative, a humectant, a feeding stimulant, an attractant, an encapsulating agent, a binder, an emulsifier, a dye, a U.V. protectant, a buffer, a flow agent, or other component to facilitate product handling and application for particular target pests.

Suitable surface-active agents include but are not limited to anionic compounds such as a carboxylate, for example, a metal carboxylate of a long chain fatty acid; an N-acylsarcosinate; mono or di-esters of phosphoric acid with fatty alcohol ethoxylates or salts of such esters; fatty alcohol sulphates such as sodium dodecyl sulphate, sodium octadecyl sulphate or sodium cetyl sulphate; ethoxylated fatty alcohol sulphates; ethoxylated alkylphenol sulphates; lignin sulphonates; petroleum sulphonates; alkyl aryl sulphonates such as alkyl-benzene sulphonates or lower alkylnaphthalene sulphonates, e.g. butyl-naphthalene sulphonate; salts of sulphonated naphthalene-formaldehyde condensates; salts of sulphonated phenol-formaldehyde condensates; or more complex sulphonates such as the amide sulphonates, e.g. the sulphonated condensation product of oleic acid and N-methyl taurine or the dialkyl sulphosuccinates, e.g. the sodium sulphonate or dioctyl succinate. Non-ionic agents include condensation products of fatty acid esters, fatty alcohols, fatty acid amides or fatty-alkyl- or alkenyl-substituted phenols with ethylene oxide, fatty esters of polyhydric alcohol ethers, e.g. sorbitan fatty acid esters, condensation products of such esters with ethylene oxide, e.g. polyoxyethylene sorbitar fatty acid esters, block copolymers of ethylene oxide and propylene oxide, acetylenic glycols such as 2,4,7,9-tetraethyl-5-decyn-4,7-diol, or ethoxylated acetylenic glycols. Examples of a cationic surface-active agent include, for instance, an aliphatic mono-, di-, or polyamine as an acetate, naphthenate or oleate; an oxygen-containing amine such as an amine oxide of polyoxyethylene alkylamine; an amide-linked amine prepared by the condensation of a carboxylic acid with a di- or polyamine; or a quaternary ammonium salt.

Examples of inert materials include but are not limited to inorganic minerals such as kaolin, phyllosilicates, carbonates, sulfates, phosphates or botanical materials such as wood products, cork, powdered corncobs, peanut hulls, rice hulls, and walnut shells.

The compositions of the present invention can be in a suitable form for direct application or as a concentrate or primary powder which requires dilution with a suitable quantity of water or other diluent before application. The insecticidal concentration will vary depending upon the nature of the particular formulation, specifically, whether it is a concentrate or to be used directly. The composition contains 1 to 98% of a solid or liquid inert carrier, and 0 to 50%, preferably 0.1 to 50% of a surfactant. These compositions will be administered at the labeled rate for the commercial product, preferably about 0.01 lb–5.0 lb per acre when in dry form and at about 0.01 pts–10 pts per acre when in liquid form.

In a further embodiment, the strains, spores, crystals, delta-endotoxins or mutants of the present invention can be treated prior to formulation to prolong the pesticidal activity when applied to the environment of a target pest as long as the pretreatment is not deleterious to the crystal delta-endotoxin. Such treatment can be by chemical and/or physical means as long as the treatment does not deleteriously affect the properties of the composition(s). Examples of chemical reagents include, but are not limited to, halogenating agents; aldehydes such as formaldehyde and glutaraldehyde; anti-infectives, such as zephiran chloride; alcohols, such as isopropranol and ethanol; and histological fixatives, such as Bouin's fixative and Helly's fixative (see, for example, Humason, Animal Tissue Techniques, W. H. Freeman and Co., 1967).

The compositions of the invention can be applied directly to the plant by, for example, spraying or dusting at the time when the pest has begun to appear on the plant or before the appearance of pests as a protective measure. Plants to be protected within the scope of the present invention include, but are not limited to, cereals (wheat, barley, rye, oats, rice, sorghum and related crops), beets (sugar beet and fodder beet), drupes, pomes and soft fruit (apples, pears, plums, peaches, almonds, cherries, strawberries, raspberries, and blackberries), leguminous plants (alfalfa, beans, lentils, peas, soybeans), oil plants (rape, mustard, poppy, olives, sunflowers, coconuts, castor oil plants, cocoa beans, groundnuts), cucumber plants (cucumber, marrows, melons), fibre plants (cotton, flax, hemp, jute), citrus fruit (oranges, lemons, grapefruit, mandarins), vegetables (spinach, lettuce, asparagus, cabbages and other brassicae, carrots, onions, tomatoes, potatoes, paprika), lauraceae (avocados, cinnamon, camphor), deciduous trees and conifers (e.g. linden-trees, yew-trees, oak-trees, alders, poplars, birch-trees, firs, larches, pines), or plants such as maize, turf plants, tobacco, nuts, coffee, sugar cane, tea, vines, hops, bananas and natural rubber plants, as well as ornamentals. In most cases, the preferred mode of application is by foliar spraying. The preferred mode of application for soil pests is by furrow application or by "lay-by" application. It is generally important to obtain good control of pests in the early stages of plant growth as this is the time when the plant can be most severely damaged. The spray or dust can conveniently contain another pesticide if this is thought necessary. In a preferred embodiment, the compositions of the invention is applied directly to the plant.

The compositions of the present invention may be effective against pests including, but not limited to, pests of the order Lepidoptera, e.g. *Achroia grisella, Acleris gloverana, Acleris variana, Adoxophyes orana, Agrotis ipsilon, Alabama argillacea, Alsophila pometaria, Amyelois transitella, Anagasta kuehniella, Anarsia lineatella, Anisota senatoria, Antheraea pernyi, Anticarsia gemmatalis*, Archips sp., Argyrotaenia sp., *Athetis mindara, Bombyx mori, Bucculatrix thurberiella, Cadra cautella*, Choristoneura sp., *Cochylis hospes, Colias eurytheme, Corcyra cephalonica, Cydia latiferreanus, Cydia pomonella, Datana integerrima, Dendrolimus sibericus, Desmia funeralis, Diaphania hyalinata, Diaphania nitidalis, Diatraea grandiosella, Diatraea saccharalis, Ennomos subsignaria, Eoreuma loftini, Ephestia elutella, Erannis tiliaria, Estigmene acrea, Eulia salubricola, Eupoecilia ambiguella, Euproctis chrysorrhoea, Euxoa messoria, Galleria mellonella, Grapholita molesta, Harrisina americana, Helicoverpa subflexa, Helicoverpa zea, Heliothis virescens, Hemileuca oliviae, Homoeosoma electellum, Hyphantria cunea, Keiferia lycopersicella, Lambdina fiscellaria fiscellaria, Lambdina fiscellaria lugubrosa, Leucoma salicis, Lobesia botrana, Loxostege sticticalis, Lymantria dispar, Macalla thyrsisalis*, Malacosoma sp., *Mamestra brassicae, Mamestra configurata, Manduca quinquemaculata, Manduca sexta, Maruca testulalis, Melanchra picta, operophtera brumata*, Orgyia sp., *Ostrinia nubilalis, Paleacrita vernata, Papilio cresphontes, Pectinophora gossypiella, Phryganidia californica, Phyllonorycter blancardella, Pieris napi, Pieris rapae, Plathypena scabra, Platynota flouendana, Platynota sultana, Platyptilia carduidactyla, Plodia interpunctella, Plutella xylostella, Pontia protodiae, Pseudalotia unipuncta, Pseudoplusia includens, Sabulodes aegrotata, Schizura concinna, Sitotroga cerealella, Spilonota ocellana*, Spodoptera sp., *Thaurnstopoea pityocampa, Tineola bisselliella, Trichoplusia ni, Udea rubigalis, Xylomyges curialis, Yponomeuta padella*; Coleoptera, e.g., Leptinotarsa sp., *Acanthoscelides obtectus, Callosobruchus chinensis, Epilachna varivestis, pyrrhalta luteola, Cylas formicarius elegantulus, Listronotus oregonensis*, Sitophilus sp., *Cyclocephala borealis,*

*Cyclocephala immaculata, Macrodactylus subspinosus, Popillia japonica, Rhizotrogus majalis, Alphitobius diaperinus, Palorus ratzeburgi, Tenebrio molitor, Tenebrio obscurus, Tribolium castaneum, Tribolium confusum, Tribolius destructor.*

In specific embodiments, a composition comprising the 130,000 dalton delta-endotoxins and/or the two 33,000 dalton delta-endotoxins is effective against lepidopteran pests. Compositions comprising the strains of the present invention are also effective against lepidopteran and coleopteran pests.

The following examples are presented by way of illustration, not by way of limitation.

6. EXAMPLES

6.1. Example 1: Cultivating *B.t.* Strains EMCC0075 and EMCC0076

Subcultures of EMCC0075 and EMCC0076, maintained on Nutrient Broth Agar slants, are used to inoculate 250 ml baffled shake flasks containing 50 ml of medium with the following composition:

| | |
|---|---|
| Corn Steep liquor | 15 g/l |
| Maltrin-100 | 40 g/l |
| Potato Starch | 30 g/l |
| $KH_2PO_4$ | 1.77 g/l |
| $K_2HPO_4$ | 4.53 g/l |

The pH of the medium is adjusted to 7.0 using 10 N NaOH.

After inoculation, shake flasks are incubated at 30° C. on a rotary shaker with 250 rpm shaking for 72 hours. The *B.t.* crystals and spores, obtained in the above fermentation, are recovered by centrifugation at 15,000 rpm for 15 minutes using a Sorvall RC-5B centrifuge.

6.2. Example 2: Testing of *B.t.* Strains EMCC0075 and EMCC0076 Spores and Crystals EMCC0075 and EMCC0076 are cultivated in shake flasks as described in Example 1, supra. To determine if EMCC0075 and EMCC0076 are active against lepidopteran pests, a 1:50 dilution of culture broth is made. 5 ml of such diluted culture broth is transferred into a 50 ml polypropylene centrifuge tube. 20 ml of artificial insect diet containing antibiotics is added into the centrifuge tube. The mixture is subsequently dispensed into bioassay trays. Three to six eggs either of beet armyworm (*Spodoptera exigua*) or tobacco budworm (*Heliothis virescens*) are applied on the surface of the "diet". Mylar is ironed onto the bioassay trays and the trays are incubated at 28° C. Scoring is carried out at 7 and 11 days.

To determine if EMCC0075 and EMCC0076 are active against insect pests of the order Coleoptera, 5 ml of the culture broths are removed from the shake flasks and transferred directly into the 50 ml polypropylene centrifuge tubes. 20 ml of artificial insect diet (containing known antibiotics) are then added into the tubes (final testing concentration=20% w/w) and mixed vigorously. The mixtures are then dispensed into bioassay trays. Three to six eggs of corn rootworm (*Diabrotica undecimpunctata*) are applied to the surface of the "diet". Mylar is ironed onto the bioassay trays and the trays are incubated at 28° C. Scoring is carried out at 7 and 11 days.

The bloactivity of EMCC0075 and EMCC0076 towards *Spodoptera exigua* and *Diabrotica undecimpunctata* is expressed in terms of stunt score (SS). The stunt score is determined after incubating the trays for 7 days. In this system, 4=full size larvae (control larvae); 3=¾ size of control larvae; 2=½ size of control larvae; 1=¼ size of control larvae; and 0=mortality. The smaller the number, the higher the *B.t.* activity. The results are shown in Table I. It is evident that EMCC0075 and EMCC0076 possess activity against both lepidopteran and coleopteran pests.

TABLE I

| | *Spodoptera exigua* | *Diabrotica undecimpunctata* | *Heliothis virescens* |
|---|---|---|---|
| EMCC0075 | 1.7 | 0.9 | 1.5 |
| EMCC0076 | 1.8 | 1.8 | 1.8 |
| Control | 4.0 | 4.0 | 4.0 |

6.3. Example 3: cry Gene Profile for EMCC0075 and EMCC0076

The cry gene profile for EMCC0075 and EMCC0076 is determined by using the PCR method which is described in the Perkin Elmer Cetus Gene Amp® PCR Reagent Kit literature. Double-stranded DNA is heat-denatured and the two oligonucleotides corresponding to the cryIA(a) gene (listed in the Sequence Listing as SEQ ID NO:3 and SEQ ID NO:4 respectively), cryIA(b) gene (listed in the Sequence Listing as SEQ ID NO:5 and SEQ ID NO:6 respectively), cryIA (c) gene (listed in the Sequence Listing as SEQ ID NO:7 and SEQ ID NO:8 respectively), cryID gene (listed in the Sequence Listing as SEQ ID NO:9 and SEQ ID NO:10 respectively), cryIIIA gene (listed in the Sequence Listing as SEQ ID NO:11 and SEQ ID NO:12 respectively), cryIIIB gene (listed in the Sequence Listing as SEQ ID NO:13 and SEQ ID NO:14 respectively), cryIIIC gene (listed in the Sequence Listing as SEQ ID NO:15 and SEQ ID NO:16 respectively), and cryIIID gene (listed in the Sequence Listing as SEQ ID NO:17 and SEQ ID NO:18 respectively), are annealed at low temperature and then extended at an intermediate temperature.

PCR analysis indicated that both strains contain a cryID-like gene. A probe specific to cryID also detected a cryID-like gene in Southern analysis of restricted genomic DNA from both strains. No PCR amplifications are observed with primers to cryIA(a), cryIA(b), cryIA(c), cryIB (SEQ ID NOS:22 and 23), cryIC (SEQ ID NOS:24 and 25), cryID, cryIE (SEQ ID NOS:26 and 27), cryIF (SEQ ID NOS:28 and 29), or cryIG (SEQ ID NOS:30 and 31), nor to cryIIA (SEQ ID NOS:32 and 33), cryIIB (SEQ ID NOS:34 and 33), or cryIIC (SEQ ID NOS: 35 and 36), nor to cryIIIA, cryIIIB, cryIIIC, or cryIIID. However, Southern analysis of a restriction fragment from genomic DNA from EMCC0075 and EMCC0076 with a probe that can detect cryIA(a), cryIA(b), and cryIA(c) confirmed the presence of a cryIA-like gene.

6.4. Example 4: Purification of EMCC0075 Bipyramidial and Rhomboidal Crystals A subculture of EMCC0075, maintained on a Nutrient Broth agar plate, is used to inoculate a 2.0 liter baffled shake flask containing 500 ml of medium with the same composition as described in Example 5, infra. After inoculation, the shake flask is incubated at 30° C. on a rotary shaker for 72 hours at 250 rpm. The crystals and spores are recovered by centrifugation at 10,000 rpm (Sorvall GSA rotor) for 30 minutes. The pellets are washed with deionized water, centrifuged at 15,000 rpm (Sorvall SS34 rotor), and resuspended in deionized water by sonication to a concentration of 0.1 g wet weight per ml. 1 g wet weight crude crystals are diluted to 33.2 ml with deionized water and placed in a 250 ml separatory funnel. The bottom phase solution comprised of 10 ml 3M sodium chloride, 23.4 ml 20% polyethylene glycol 8000, and 33.4 ml 20% sodium dextran sulfate is added to the 250 ml separatory funnel and mixed, followed by 100 ml of a polyethylene glycol upper phase solution comprised of 0.3 g sodium dextran sulfate, 70.3 g polyethylene glycol 8000, and 17.5 g sodium chloride per liter deionized water. The suspension is shaken vigorously, and the two phases are allowed to separate at room temperature for 30 minutes.

The upper phase which contains large quantities of spores is removed with a pipet. The lower phase contains crystals and residual spores. The extraction is repeated several times until the upper phase contains essentially no spores. The lower phase is then diluted with 100 ml deionized water, and centrifuged at 10,000 rpr (Sorvall GSA rotor) for 45 minutes at 5° C. to recover the crystals. The recovered crystals are washed with 200 ml deionized water, and recentrifuged as before. The spores from the upper phase are also recovered using the above washing procedure.

The bipyramidal and rhomboidal crystals are then further purified by density gradient centrifugation using a discontinuous Ludox™ HS-40 (DuPont) gradient comprised of 3.8 ml each of 75%, 50%, and 38% Ludoxk™ v/v adjusted to pH 2.5 with 0.2M Tris-HCl. 10 mg of crystals in 100 µl deionized water are layered on the top of the gradient, and centrifuged in a Beckman Ultracentrifuge at 10,000 rpm (Beckman 41 Ti rotor) for 15 minutes at 20° C. Four separate bands are obtained. One contains pure rhomboidal crystals and another contains pure bipyramidal crystals. The two other bands contains mixtures of the two crystal types. The pure crystal bands are recovered, washed with deionized water, and used for bioassay.

6.5. Example 5: SDS-PAGE Analysis of the Delta-endotoxins from EMCC0075 and EMCC0076

Subcultures of EMCC0075 and EMCC0076, maintained on Nutrient Broth agar plates, are used to inoculate 250 ml baffled shake flasks containing 50 ml of medium with the following composition:

| | |
|---|---|
| Glucose | 2.0 g/l |
| $KH_2PO_4$ | 0.86 g/l |
| $K_2HPO_4$ | 0.55 g/l |
| Sodium Citrate | 2.0 g/l |
| $CaCl_2$ | 0.1 g/l |
| $MnCl_2.4H_2O$ | 0.16 g/l |
| $MgCl_2.6H_2O$ | 0.43 g/l |
| $ZnCl_2$ | 0.007 g/l |
| $FeCl_3$ | 0.003 g/l |
| Casamino Acids | 5 g/l |

After inoculation, the shake flasks are incubated at 30° C. on a rotary shaker for 72 hours at 250 rpm. The *B.t.* crystals obtained in the above fermentations of EMCC0075 and EMCC0076 are recovered by centrifugation at 10,000 rpm (Sorvall GSA rotor) for 30 minutes. The *B.t.* crystals are then purified by biphasic extraction using sodium dextran sulfate and polyethylene glycol as outlined in Example 4, supra.

*B.t.* crystal preparations from EMCC0075 and EMCC0076 are analyzed by SDS-PAGE. Specifically, the SDS-PAGE is carried out on 10–15% gradient gels using Pharmacia's Phast System™. The protein bands are analyzed on a Pharmacia densitometer using Pharmacia Gelscan™ Software. The results indicated that the crystals produced by both strains contain at least two proteins with molecular weights of approximately 130,000 daltons and 33,000 daltons.

6.6. Example 6: Bioassay using *Spodoptera exigua* to Determine Activity of Novel Lepidopteran Active *Bacillus thuringiensis* Strains To determine if purified bipyramidal and rhomboidal crystals are active against lepidopteran pests, the crystals are bioassayed against *Spodoptera exigua* using a surface overlay assay. Samples of crystal preparations are applied to individual wells of a jelly tray containing 500 µl of solidified artificial insect diet per well. The trays containing the various samples are air dried. Two to four 2nd or early 3rd instar *Spodoptera exigua* are added to each well containing the dried test sample. The trays are then sealed with Mylar punched with holes for air exchange and are incubated for 3 days at 30° C. The degree of stunting, as described in Example 2, supra, is then recorded.

The results are shown in Table II. It is evident that, surprisingly, both the bipyramidal crystal and the rhomboidal crystal possess activity against *Spodoptera exigua*. The spores also show activity against *Spodoptera exigua*.

TABLE II

| Sample | Wet Weight | Stunt score |
|---|---|---|
| No crystals or spores | — | 4 |
| Rhomboidal & bipyramidal crystals and spores | 2.5 mg/well | 1 |
| | 5.0 mg/well | 0–1 |
| Both crystals, no spores | 2.5 mg/well | 1 |
| | 10 mg/well | 0–1 |
| Bipyramidal crystals | 0.092 mg/well | 1 |
| | 0.48 mg/well | 0–1 |
| Rhomboidal crystals | 0.05 mg/well | 1 |
| | 0.1 mg/well | 0–1 |
| | 0.5 mg/well | 0 |
| Spores | 10 mg/well | 0–1 |
| | 20 mg/well | 0 |

6.7. Example 7: Bioassay agains *Diabrotica undecimpunctata*

The coleopteran activity or the whole culture broth of EMCC0075, prepared as described in EXAMPLE 1, is bioassayed against *Diabrotica undecimpunctata* using a micro-diet incorporation bioassay. Specifically, artificial diet is prepared comprised of water, agar, sugar, casein, wheat germ, methyl paraben, sorbic acid, linseed oil, cellulose, salts, propionic acid, phosphoric acid, streptomycin, chlortetracycline, and vitamins. The artificial diet is developed to allow samples consisting of rehydrated dry powders and liquids to be incorporated at a rate of 20% v/v. The test sample is prepared in microcentrifuge tubes to yield eight serial dilutions. The whole broth sample is tested neat at 200 µl/ml, and then diluted in 0.1% Tween 20™ to contain 132 µl/ml, 87 µl/ml, 66 µl/ml, 44 µl/ml, 30 µl/ml, 20 µl/ml, and 13 µl/ml. The molten mixture is vortexed and pipetted in 0.1 ml aliquots into 10 wells of a 96 well microtiter plate. Control samples containing 0.1% Tween 20™ are dispensed into 16 wells. Once the diet has cooled and solidified, two neonate *Diabrotica undecimpunctata* larvae are added to each well, and the trays are covered with a perforated sheet of clear mylar. The trays are then incubated for five days at 28±2° C. and 65% relative humidity.

After five days, insect mortality is rated. The mylar sheet is removed and each well of the microtiter plate is inspected using a dissecting microscope. Larvae that do not move when prodded with a dissecting needle are counted as dead. Percent mortality is calculated, and the data is analyzed via parallel probit analysis. The $LC_{50}$, $LC_{90}$, slope of regression lines, coefficient of variation (CV), and potencies are determined.

The results as shown in Table III indicate the whole culture broth from EMCC-0075 has a $LC_{50}$ and a $LC_{90}$ of 51 μl/ml diet and 170 μl/ml diet, respectively, against *Diabrotica undecimpunctata*.

TABLE III

| $LC_{50}$ | $LC_{90}$ | Slope | CV | N |
|---|---|---|---|---|
| μl/ml | μl/ml | | | |
| 51 | 170 | 2 | 7 | 8 |

6.8. Example 8: Protein Sequencing of the Delta-endotoxins from the Rhomboidal Crystal Proteins of EMCC0075

60 μl of 50% trifluoroacetic acid (TFA) are added to 25 μg of rhomboidal crystals. Four 15 μl aliquots of the mixture are spot dried onto a Biobrene-coated and TFA-pretreated microcartridge glass fiber filter. N-terminal sequencing is performed on a Applied Biosystems Inc. Protein Sequencer Model 476A with on-line HPLC and liquid phase TFA delivery. HPLC determination of phenylthiohydantoin-amino acids is achieved by using the Premix buffer system (ABI Inc.). Data is collected on a Macintosh IIsi using ABI's 610 data analysis software.

A double sequence is observed at approximately a 60/40 ratio. Data are analyzed and the sequences are sorted as follows:

"MIVDL": MIVDLYRYLGGLAAVNAVLHFYEPRP (SEQ ID NO:1)

"MKHHK": MKHHKNFDHI (SEQ ID NO:2)

6.9. Example 9: Cloning of the Genes Encoding the "MIVDL" and "MKHHK" Proteins The amino acid sequence initially determined for the "MIVDL" protein, MIVDLYRYLGGLAAVNAVLHFYEPRP, is encoded by the sequence ATG ATH GTN GAY YTN TAY MGN TAY YTN GGN GGN YTN GCN GCN GTN AAY GCN GTN YTN CAY TTY TAY GAR CCN MGN CCN (SEQ ID NO:19). Based on this sequence, a 71 nt oligomer is designed, where mixed deoxynucleotides are used at the 2-fold redundant positions and deoxyinosine at the 4-fold redundant positions to decrease both base discrimination at mismatches and selectivity at incorrect bases (Martin, F. H., and M. M. Castro, 1985, Nucleic Acids Res. 13: 892–8938): ATG ATI GTI GAY YTI TAY MGI TAY YTI GGI GGI YTI GCI GCI GTI AAY GCI GTI YTI CAY TTY TAY GAR CC (SEQ ID NO:20).

The amino acid sequence determined for the "MKHHK" protein, namely, MKHHKNFDHI, permitted design of a more discriminating probe because of the absence of amino acids specified by more than two codons. Further discrimination is permitted by the assumption that As or Ts would be used in the coding sequence in preference to Gs or Cs, due to the overall low % G+C content of *B. t.* strains (approx 34 moles %, Claus, D., and R. C. W. Berkeley. 1986. Genus Bacillus, p. 1112. In P. H. A. Sneath (ed.), Bergey's manual of systematic bacteriology, v. 2. The Williams and Wilkins Co., Baltimore). The following probe is synthesized: ATG AAA CAT AAA AAT TTT GAT CAT AT (SEQ ID NO:21). Both the MIVDL and the MKHHK probes are tailed with digo,xygenin-dUTP according to the manufacturer's instructions (Boerhinger-Mannheim Genius System™ Users Guide, Version 2.0).

BMCC0075 genomic DNA is digested with EcoRI, EcoRV, HindIII, PstI, or combinations of those enzymes overnight in buffers supplied by the manufacturers, electrophoresed through 0.8% agarose in 0.5× TBE (TRIS-borate-EDTA buffer; Sambrook et al., 1989, in Molecular Cloning, a Laboratory manual. Cold Spring Laboratory Press, Cold Spring Harbor, N.Y.), transfer-red in 10× SSC to Boehringer Mannheim nylon membrane with a Stratagene Posiblotter in 10× SSC, and then probed as described below. The MIVDL probe, after hybridization and stringent washing at 48° C. with 0.5× SSC, detected EcoRV and PstI fragments 12 kb or more in size, an EcoRI fragment of approx 10 kb, and a HindIII fragment of approx 3.5 kb. The MKHHK probe, after hybridization and stringent washing at 48° C. with 5× SSC, detected the same size EcoRI, EcoRV, and PstI fragments as did the MIVDL probe. This result indicates that the two genes lie in close proximity to each other. Additionally, the MKHHK probe detected a HindIII fragment of approx 6 kb.

To clone the HindIII fragments encoding at least part of the "MIVDL" and "MKHHK" proteins, pUC118 is digested with HindIII, and then treated with calf intestinal phosphatase to dephosphorylate the 5' ends and thus prevent vector religation. Restricted and phosphatased pUC118 is then mixed with EMCC0075 genomic DNA that had been previously digested to completion with HindIII. After ligation, the reaction mix is used to transform *E. coli* strain XL1-Blue MRF' (Stratagene, Inc., La Jolla, Calif.). Colonies harboring the desired DNA fragment are detected by "colony hybridization" with the aforementioned "MIVDL" and "MKHHK" probes by the procedure described by Sambrook et al., 1989, Molecular cloning, A Laboratory Manual, Cold Spring Laboratory Press, Cold Spring Harbor, N.Y. Three fragments are cloned with the "MIVDL" and "MKHHK" probes (see FIG. 2). *E. coli* containing the "13D" MIVDL gene fragment aew referred to as EMCC0117 cells; *E. coli* containing the "8D-1" MKHHK gene fragment are referred to as EMCC0118 cells; *E. coli* containing the "2B" fragment of the MIVDL and MKHHK genes are referred to as EMCC0118 cells.

6 .10. Example 10: Sequencing of the Genes Encoding the "MIDVDL" and "MKHHK" Proteins Nested deletions of three cloned fragments described in EXAMPLE 9 are performed according to the method of Henikoff (*Gene* 28:351–359, 1984) with a Promega "Erase-a-Base" kit. Nested deletion sets encompassing the region of interest are sequenced by the dideoxy method (Sanger et al., 1977, *PNAS* USA 74:5463–5467) with an ABI 373A sequencer. Sequence correction is performed with SeqEd v 1.0.3; sequence is assembled with MacVector 4.1.1 and AssemblyLIGN v 1.0.7; and additional alignments and searches are performed with the IntelliGenetics Suite Programs, v 5.4.

The determined nucleotide (nt) sequence encoding the MKHHK and MIVDL proteins are shown in SEQ ID NO:39 and 40. The deduced amino acid sequence of the MKHHK and MIVDL proteins is shown underneath their corresponding DNA sequence. The amino acid sequence determined by N-terminal Edman degradation as described in. EXAMPLE 8 is in complete agreement with the sequences deduced from the nucleotide sequence. The genomic DNA sequence is shown in SEQ ID NOS:41 (MKHHK and MIVDL), 44 (MKHHK), and 45 (MIVDL).

The MKHHK and MIVDL genes encode proteins with calculated molecular masses of 32,719 and 32,866 daltons. The MKHHK protein aligns poorly with any deduced protein from the EMBL, GeneSeq, or GenBank sequence databases. The MIVDL protein has weak regional homology with the 34 kdal gene of *B. thuringiensis* subsp. *thompsoni* as shown in FIG. 3 (SEQ ID NO:42) (Brown and Whiteley, 1990, *J. Bacteriology* 174:549–557). In addition, the MIVDL protein has weak regional homologies with CryIA (a) (SEQ ID NO:43) (see FIG. 3). These weak homologies do not correspond to the any of the 5 conserved blocks of Cry toxins described by Höfte and Whiteley (*Microbiol. Rev.* 53:242–255, 1989).

A nucleotide analysis of the region encoding the MKHHK and MIVDL genes shows ribosome binding sites (AAGGAGT and AAGGTGG, respectively) that differ by one nucleotide with the canonical ribosome binding site of *B. subtilis* (AAGGAGG, which is presumably similar to the *B. thuringiensis* RBS). There is a reasonable transcriptional terminator downstream of the MIVDL gene.

7. DEPOSIT OF MICROORGANISMS

The following strains of *Bacillus thuringiensis* have been deposited in the Agricultural Research Service Patent Culture Collection Laboratory (NRRL), Northern Regional Research Center, 1815 University Street, Peoria, Ill. 61604, USA.

| Strain | Accession Number | Deposit Date |
| --- | --- | --- |
| EMCC0075 | NRRL B-21019 | Dec. 3, 1992 |
| EMCC0076 | NRRL B-21020 | Dec. 3, 1992 |

The strains have been deposited under conditions that assure that access to the culture will be available during the pendency of this patent application to one determined by the Commissioner of Patents and Trademarks to be entitled thereto under 37 C.F.R. §1.14 and 35 U.S.C. §122 and under conditions of the Budapest Treaty. The deposit represents a biologically pure culture of each deposited strain. The deposit is available as required by foreign patent laws in countries wherein counterparts of the subject application, or its progeny are filed. However, it should be understood that the availability of a deposit does not constitute a license to practice the subject invention in derogation of patent rights granted by governmental action.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

Various references are cited herein, the disclosures of which are incorporated by reference in their entireties.

What is claimed is:

1. A biologically pure *Bacillus thuringiensis* strain or spores, crystals or mutants thereof having insecticidal activity against an insect pest of the order Lepidoptera and an insect pest of the order Coleptera, which strain or mutants produce one delta-endotoxin having a molecular weight of about 33,000 daltons and an amino acid sequence as depicted in SEQ ID NO:37 and one delta-endotoxin having a molecular weight of about 33,000 daltons and an amino acid sequence as depicted in SEQ ID NO:38 and at least two delta-endotoxins having a molecular weight of about 130,000 daltons in which said delta-endotoxins have insecticidal activity against an insect pest of the order Lepidoptera.

2. An insecticidal composition comprising the biologically pure *Bacillus thuringiensis* strain of claim 1 in association with an insecticidal carrier.

* * * * *

```
                       SEQUENCE LISTING

<160> NUMBER OF SEQ ID NOS: 45

<210> SEQ ID NO 1
<211> LENGTH: 26
<212> TYPE: PRT
<213> ORGANISM: Bacillus thuringiensis

<400> SEQUENCE: 1

Met Ile Val Asp Leu Tyr Arg Tyr Leu Gly Gly Leu Ala Ala Val Asn
1               5                   10                  15

Ala Val Leu His Phe Tyr Glu Pro Arg Pro
            20                  25

<210> SEQ ID NO 2
<211> LENGTH: 10
<212> TYPE: PRT
<213> ORGANISM: Bacillus thuringiensis

<400> SEQUENCE: 2

Met Lys His His Lys Asn Phe Asp His Ile
1               5                   10

<210> SEQ ID NO 3
<211> LENGTH: 20
<212> TYPE: DNA
<213> ORGANISM: Bacillus thuringiensis

<400> SEQUENCE: 3
```

-continued ctgctccagc tgcttggctc                                                 20

<210> SEQ ID NO 4
<211> LENGTH: 22
<212> TYPE: DNA
<213> ORGANISM: Bacillus thuringiensis

<400> SEQUENCE: 4
gaattatact tggttcaggc cc                                              22

<210> SEQ ID NO 5
<211> LENGTH: 22
<212> TYPE: DNA
<213> ORGANISM: Bacillus thuringiensis

<400> SEQUENCE: 5
gcacacctta cattttaaag ca                                              22

<210> SEQ ID NO 6
<211> LENGTH: 27
<212> TYPE: DNA
<213> ORGANISM: Bacillus thuringiensis

<400> SEQUENCE: 6
agattacaag cggataccaa catcgcg                                         27

<210> SEQ ID NO 7
<211> LENGTH: 21
<212> TYPE: DNA
<213> ORGANISM: Bacillus thuringiensis

<400> SEQUENCE: 7
tggcactttc aaaataacca a                                               21

<210> SEQ ID NO 8
<211> LENGTH: 26
<212> TYPE: DNA
<213> ORGANISM: Bacillus thuringiensis

<400> SEQUENCE: 8
gcatcggata gtattactca aatccc                                          26

<210> SEQ ID NO 9
<211> LENGTH: 22
<212> TYPE: DNA
<213> ORGANISM: Bacillus thuringiensis

<400> SEQUENCE: 9
cgctctaaca tagaccttat aa                                              22

<210> SEQ ID NO 10
<211> LENGTH: 26
<212> TYPE: DNA
<213> ORGANISM: Bacillus thuringiensis

<400> SEQUENCE: 10
gacatttcat tagggcttat taattt                                          26

<210> SEQ ID NO 11
<211> LENGTH: 22
<212> TYPE: DNA
<213> ORGANISM: Bacillus thuringiensis

<400> SEQUENCE: 11
cagcggacgg ccagaccgca ag                                          22

<210> SEQ ID NO 12
<211> LENGTH: 24
<212> TYPE: DNA
<213> ORGANISM: Bacillus thuringiensis

<400> SEQUENCE: 12
gtcggagtca acaaccttag gggc                                        24

<210> SEQ ID NO 13
<211> LENGTH: 21
<212> TYPE: DNA
<213> ORGANISM: Bacillus thuringiensis

<400> SEQUENCE: 13
atccggaaaa gccgctatgt c                                           21

<210> SEQ ID NO 14
<211> LENGTH: 21
<212> TYPE: DNA
<213> ORGANISM: Bacillus thuringiensis

<400> SEQUENCE: 14
atccggaaaa gccgctatgt c                                           21

<210> SEQ ID NO 15
<211> LENGTH: 24
<212> TYPE: DNA
<213> ORGANISM: Bacillus thuringiensis

<400> SEQUENCE: 15
ggccagaaaa tggaaaaatt tggg                                        24

<210> SEQ ID NO 16
<211> LENGTH: 21
<212> TYPE: DNA
<213> ORGANISM: Bacillus thuringiensis

<400> SEQUENCE: 16
gtgggtacag gaggtaccaa a                                           21

<210> SEQ ID NO 17
<211> LENGTH: 21
<212> TYPE: DNA
<213> ORGANISM: Bacillus thuringiensis

<400> SEQUENCE: 17
gtgggtacag gaggtaccaa a                                           21

<210> SEQ ID NO 18
<211> LENGTH: 23
<212> TYPE: DNA
<213> ORGANISM: Bacillus thuringiensis

<400> SEQUENCE: 18
cgaaatacta tgagtgtaac tgc                                         23

<210> SEQ ID NO 19
<211> LENGTH: 78
<212> TYPE: DNA
<213> ORGANISM: Artificial Sequence
<220> FEATURE:

```
<223> OTHER INFORMATION: Degenerative sequence encoding the MIVDL
                        protein from Bacillus thuringiensis
FEATURE:
<221> NAME/KEY: modified_base
<222> LOCATION: (6)...(6)
<223> OTHER INFORMATION: at position 6
      h = a or c or t/u
<220> FEATURE:
<221> NAME/KEY: modified_base
<222> LOCATION: (12)...(66)
<223> OTHER INFORMATION: at positions 12, 13, 18, 24, 25, 34, 48, 55,
                        60, 63 and 66 y = t/u or c
<220> FEATURE:
<221> NAME/KEY: modified_base
<222> LOCATION: (14)...(78)
<223> OTHER INFORMATION: at positions 9, 15, 21, 27, 30, 33, 36, 39, 42,
                        45, 51, 54, 57, 72, 75, and 78 n = a or g or c
                        or t/u, unknown, or other
<220> FEATURE:
<221> NAME/KEY: modified_base
<222> LOCATION: (69)...(69)
<223> OTHER INFORMATION: r = g or a
<220> FEATURE:
<221> NAME/KEY: modified_base
<222> LOCATION: (19)...(19)
<223> OTHER INFORMATION: m = a or c
<220> FEATURE:
<221> NAME/KEY: modified_base
<222> LOCATION: (73)...(73)
<223> OTHER INFORMATION: m = a or c

<400> SEQUENCE: 19
atgathgtng ayytntaymg ntayytnggn ggnytngcng cngtnaaygc ngtnytncay      60
ttytaygarc cnmgnccn                                                   78

<210> SEQ ID NO 20
<211> LENGTH: 71
<212> TYPE: DNA
<213> ORGANISM: Artificial Sequence
<220> FEATURE:
<223> OTHER INFORMATION: Oligonucleotide probe
<220> FEATURE:
<221> NAME/KEY: modified_base
<222> LOCATION: (6)...(57)
<223> OTHER INFORMATION: at positions 6, 9, 15, 21, 27, 30, 33, 36, 39,
                        42, 45, 51, 54, and 57 n = inosine
<220> FEATURE:
<221> NAME/KEY: modified_base
<222> LOCATION: (12)...(66)
<223> OTHER INFORMATION: at positions 12, 13, 18, 24, 25, 34, 48, 55,
                        60, 63, and 66 y = t/u or c
<220> FEATURE:
<221> NAME/KEY: modified_base
<222> LOCATION: (19)...(19)
<223> OTHER INFORMATION: m = a or c
<220> FEATURE:
<221> NAME/KEY: modified_base
<222> LOCATION: (69)...(69)
<223> OTHER INFORMATION: r = g or a

<400> SEQUENCE: 20
atgatngtng ayytntaymg ntayytnggn ggnytngcng cngtnaaygc ngtnytncay      60
ttytaygarc c                                                          71

<210> SEQ ID NO 21
<211> LENGTH: 26
<212> TYPE: DNA
<213> ORGANISM: Bacillus thuringiensis

<400> SEQUENCE: 21
atgaaacata aaatttttga tcatat                                          26
```

-continued

<210> SEQ ID NO 22
<211> LENGTH: 31
<212> TYPE: DNA
<213> ORGANISM: Bacillus thuringiensis

<400> SEQUENCE: 22
ttgaattcat atctactaat gagcaatcga a                              31

<210> SEQ ID NO 23
<211> LENGTH: 22
<212> TYPE: DNA
<213> ORGANISM: Bacillus thuringiensis

<400> SEQUENCE: 23
ccacacgcct agattctcat gc                                        22

<210> SEQ ID NO 24
<211> LENGTH: 46
<212> TYPE: DNA
<213> ORGANISM: Bacillus thuringiensis

<400> SEQUENCE: 24
cgggatccac agttacagtc tgtagctcaa ttacctactt ttaacg              46

<210> SEQ ID NO 25
<211> LENGTH: 23
<212> TYPE: DNA
<213> ORGANISM: Bacillus thuringiensis

<400> SEQUENCE: 25
ggccaaggtt gctgtaataa tcg                                       23

<210> SEQ ID NO 26
<211> LENGTH: 24
<212> TYPE: DNA
<213> ORGANISM: Bacillus thuringiensis

<400> SEQUENCE: 26
ctcaatattc tcgaagctgg ggcc                                      24

<210> SEQ ID NO 27
<211> LENGTH: 23
<212> TYPE: DNA
<213> ORGANISM: Bacillus thuringiensis

<400> SEQUENCE: 27
gcagtctgta cggaatttat aca                                       23

<210> SEQ ID NO 28
<211> LENGTH: 22
<212> TYPE: DNA
<213> ORGANISM: Bacillus thuringiensis

<400> SEQUENCE: 28
cgagggttag cagatagcta tg                                        22

<210> SEQ ID NO 29
<211> LENGTH: 21
<212> TYPE: DNA
<213> ORGANISM: Bacillus thuringiensis

<400> SEQUENCE: 29
aagatggggc ggtctaactc c                                         21

<210> SEQ ID NO 30
<211> LENGTH: 24
<212> TYPE: DNA
<213> ORGANISM: Bacillus thuringiensis

<400> SEQUENCE: 30
gaccgttatc gggtgaatct ttag                                    24

<210> SEQ ID NO 31
<211> LENGTH: 24
<212> TYPE: DNA
<213> ORGANISM: Bacillus thuringiensis

<400> SEQUENCE: 31
tcggctgcac tctaaattgt tgag                                    24

<210> SEQ ID NO 32
<211> LENGTH: 22
<212> TYPE: DNA
<213> ORGANISM: Bacillus thuringiensis

<400> SEQUENCE: 32
tattgagtga attatgggggg at                                     22

<210> SEQ ID NO 33
<211> LENGTH: 23
<212> TYPE: DNA
<213> ORGANISM: Bacillus thuringiensis

<400> SEQUENCE: 33
atgttctaaa ttctaacata tcg                                     23

<210> SEQ ID NO 34
<211> LENGTH: 22
<212> TYPE: DNA
<213> ORGANISM: Bacillus thuringiensis

<400> SEQUENCE: 34
ttatacctag atcctattgt tg                                      22

<210> SEQ ID NO 35
<211> LENGTH: 23
<212> TYPE: DNA
<213> ORGANISM: Bacillus thuringiensis

<400> SEQUENCE: 35
taacatttcc acactttca atc                                      23

<210> SEQ ID NO 36
<211> LENGTH: 19
<212> TYPE: DNA
<213> ORGANISM: Bacillus thuringiensis

<400> SEQUENCE: 36
aaggctagcg actgctgtc                                          19

<210> SEQ ID NO 37
<211> LENGTH: 287
<212> TYPE: PRT
<213> ORGANISM: Bacillus thuringiensis

<400> SEQUENCE: 37

-continued

Met Lys His His Lys Asn Phe Asp His Ile Val Trp Asp Phe Ala Glu
1 5 10 15

Lys Trp Thr Glu Gln Lys Gly Val Asp Leu Lys Arg Val Ser Tyr Val
20 25 30

Asp Pro Ile Thr Gly Glu Asp Thr Leu Glu Phe Ile Thr Lys Phe Asn
35 40 45

Tyr Val Gly Lys Leu Glu Glu Lys Ala Tyr Cys Pro Glu Val Ile Glu
50 55 60

Thr Gln Ser Phe Ser Asn Ser Asn Cys Asp Val Ser Arg Glu Phe Leu
65 70 75 80

Lys Lys Lys Val Asp Arg Lys Glu Cys Tyr Leu Trp Asp Ile Asp Tyr
85 90 95

Gly Phe Ile Ile Pro Thr Ser Val Leu Thr Asn Pro Leu Leu Pro Pro
100 105 110

Thr Leu Asn Glu Lys Ile Asn Pro Ala Met Glu Val Asp Leu Phe Lys
115 120 125

Ser Ala Asn Leu Phe Glu Ser Lys Leu Asn Asn Tyr Arg Met Ile Glu
130 135 140

Ala Gly Val Tyr Ile Glu Pro Asn Gln Ala Val Thr Ala Ser Ile Met
145 150 155 160

Val Thr Pro Lys Gln Val Gln Gln Asp Tyr Cys Ile Ser Leu Glu Ile
165 170 175

Ser Gly Ser Ile Ile Ile Glu Leu Lys Asp Ala Tyr Asn Ala Cys Thr
180 185 190

Asp Lys Glu Thr Ile Glu Thr Ile Phe Tyr Thr Val Pro Ile Ala Asp
195 200 205

Ile Tyr Arg Ser Glu Leu Ala His Asn His Ser Phe His Leu Asp Gly
210 215 220

Glu Thr Val Ile Phe Thr Gly Lys Gly Thr Phe Lys Gly Leu Ile Cys
225 230 235 240

Ser Asn Ile Phe Val Glu Gly Glu Arg Phe Asp Ser Gln Thr Gly Glu
245 250 255

Cys Leu Gly Lys Tyr Val Ile Pro Leu Ser Ile Glu Lys Lys Asn Asn
260 265 270

Val Asp Cys Ile Ser Ile Phe Leu Asn Ser Glu Lys Gly Gly Ile
275 280 285

<210> SEQ ID NO 38
<211> LENGTH: 294
<212> TYPE: PRT
<213> ORGANISM: Bacillus thuringiensis

<400> SEQUENCE: 38

Met Ile Val Asp Leu Tyr Arg Tyr Leu Gly Gly Leu Ala Ala Val Asn
1 5 10 15

Ala Val Leu His Phe Tyr Glu Pro Arg Pro Asp Ile Cys Arg Asn Ile
20 25 30

Ser Glu Glu Tyr Asn Leu Ile Val Phe Gly Asp Arg Ile Pro Thr Phe
35 40 45

Ser Ile Asp Pro Ser Gln Ile Asn Ile Asn Asn Leu Ser Val Asp Thr
50 55 60

Pro Val Asp Glu Ile Thr Ile Asn Asn Val Arg Ser Ile Gln Leu Ile
65 70 75 80

Ser Ser Arg Phe Glu Asn Thr Gly Phe Val Asp Thr Glu Asn Tyr Phe
85 90 95

Thr Pro Glu Leu Ser Arg Thr Val Val Asn Ser Ile Ser Thr Ser Thr
            100                 105                 110

Thr Thr Gly Tyr Lys Tyr Thr Gln Ser Leu Thr Val Ser Ser Lys Phe
        115                 120                 125

Ser Phe Asn Phe Pro Val Ala Gly Ala Glu Asn Asn Ile Ser Phe Ser
    130                 135                 140

Val Gly Phe Glu Gln Asn Leu Ser Thr Thr Glu Thr Lys Thr Glu Ser
145                 150                 155                 160

Thr Ser Thr Leu Met Arg Ile Pro Pro Gln Pro Val Ser Val Arg Pro
                165                 170                 175

Arg Thr Ala Lys Arg Val Glu Ile Ser Leu Phe Glu Leu Ala Ile Pro
            180                 185                 190

Arg Ile Gln Asn Glu Ile Ser Gly Phe Val Thr Gly Thr Leu Pro Thr
            195                 200                 205

Ile Ser Asn Ser His Ile Ser Asp Leu Tyr Ala Val Leu Thr Arg Thr
            210                 215                 220

Asp Ser Leu Cys Pro Asn Ser Tyr Ile Asn Arg Asp Asp Phe Leu Arg
225                 230                 235                 240

Ile Asp His Glu Asn Arg Gly Leu Gly Leu Gln Gly Phe Gly Ser Leu
                245                 250                 255

Thr Gly Asn Leu Thr Ser Leu Asp Phe Ala Ile Arg Thr Thr Glu Tyr
                260                 265                 270

Asp Leu Pro Ser Asn Thr Ile Ile Asn Ile Glu Asn Glu Ile Lys Arg
            275                 280                 285

Ala His Ile Leu Thr Gln
        290

<210> SEQ ID NO 39
<211> LENGTH: 864
<212> TYPE: DNA
<213> ORGANISM: Bacillus thuringiensis

<400> SEQUENCE: 39
atgaaacatc ataaaaattt tgatcacata gtttgggact tcgctgaaaa gtggactgaa      60 caaaagggg tagatttaaa aagggtcagt tatgtagatc ccattactgg tgaagataca     120
ttagagttta taaccaaatt taattatgtt gggaaattag aagaaaaagc ttattgtcca     180
gaagtaatag aaacacaatc tttttcaaac tcaaattgtg acgtttcgag ggaatttcta     240
aagaaaaaag tagacaggaa ggaatgttat ttatgggata tagactatgg gtttattata     300
ccaacttcgg tacttacaaa tccattatta cccccactc tcaatgaaaa aattaatcca     360
gcaatggaag tggacttatt taaagtgca aacctgtttg aatccaaact aaataattat     420
agaatgatag aagcaggtgt ttatattgaa ccaaatcaag cagtaaccgc cagcataatg     480
gttacaccaa acaagtaca gcaagattat tgtattagcc ttgagatttc aggtagtatt     540
atcattgagc tgaaagatgc ttataatgct tgtacagata agaaactat tgaaacaata     600 ttctataccg tgccaattgc agatatatac agatccgagc ttgcccataa ccattccttt     660
catttagatg gagaaactgt aatatttaca gggaaggta cgtttaaagg cttaatatgt     720
tctaatatat ttgttgaagg ggaaagattc gattctcaaa cggggaatg tttggggaaa     780 tatgtgatcc cattaagtat agaaaagaaa aataatgtag attgtatctc tatatttta     840 aattcagaaa aaggtgggat ttaa                                             864

<210> SEQ ID NO 40
<211> LENGTH: 885
<212> TYPE: DNA
<213> ORGANISM: Bacillus thuringiensis

<400> SEQUENCE: 40

| | | | | | |
|---|---|---|---|---|---|
| atgatagtag | atttatatag | atatttaggt | ggattggcag | cagtaaatgc | cgtacttcac | 60 |
| ttttatgagc | cacgccctga | tatatgtagg | aatataagcg | aagaatataa | ccttatagta | 120 |
| tttggagacc | gtataccaac | ttttagcata | gatccttcgc | aaataaatat | taacaattta | 180 |
| tctgtggaca | ctccagtgga | tgaaataact | attaataacg | tgagaagtat | acaattaata | 240 |
| tctagtcgtt | ttgaaaatac | aggatttgtc | gatactgaaa | attattttac | tcctgaatta | 300 |
| tctagaacag | ttgtaaatag | catatctaca | tcgactacta | caggatataa | gtacactcaa | 360 |
| tcccttactg | tttcatccaa | attctccttt | aatttcccag | ttgcgggtgc | agaaaataat | 420 |
| atttcatttt | cagtaggttt | tgaacaaaac | ctttcaacta | cagaaactaa | aacagaaagt | 480 |
| acttcaacgc | ttatgcgtat | acctccacaa | ccagtttccg | taagacccag | aacagcaaaa | 540 |
| agggttgaaa | tatcgctctt | tgaattggca | atccctagaa | tacaaaacga | aatttccgga | 600 |
| tttgtaacag | gtactcttcc | aacaatttca | aattcgcata | tttccgatct | ttatgctgta | 660 |
| ttaacacgga | ctgatagcct | atgccctaat | tcatatatta | accgagatga | cttttaaga | 720 |
| atagatcatg | aaaataggg | tttgggatta | caaggcttcg | gttctctcac | tggaaattta | 780 |
| acatcattag | attttgcaat | tagaactact | gaatatgatt | taccttcaaa | tacaattata | 840 |
| aatatagaga | acgaaataaa | aagagcccat | atactcacac | agtaa | | 885 |

<210> SEQ ID NO 41
<211> LENGTH: 2101
<212> TYPE: DNA
<213> ORGANISM: Bacillus thuringiensis

<400> SEQUENCE: 41

| | | | | | |
|---|---|---|---|---|---|
| attaaacact | aaatacattc | acattattct | aacaaagaaa | aggagtaata | attatgaaac | 60 |
| atcataaaaa | ttttgatcac | atagtttggg | acttcgctga | aaagtggact | gaacaaaagg | 120 |
| gggtagattt | aaaaagggtc | agttatgtag | atcccattac | tggtgaagat | acattagagt | 180 |
| ttataaccaa | atttaattat | gttgggaaat | tagaagaaaa | agcttattgt | ccagaagtaa | 240 |
| tagaaacaca | atctttttca | aactcaaatt | gtgacgtttc | gagggaattt | ctaaagaaaa | 300 |
| aagtagacag | gaaggaatgt | tatttatggg | atatagacta | tgggtttatt | ataccaactt | 360 |
| cggtacttac | aaatccatta | ttacccccca | ctctcaatga | aaaaattaat | ccagcaatgg | 420 |
| aagtggactt | atttaaaagt | gcaaacctgt | ttgaatccaa | actaaataat | tatagaatga | 480 |
| tagaagcagg | tgtttatatt | gaaccaaatc | aagcagtaac | cgccagcata | atggttacac | 540 |
| caaacaagt | acagcaagat | tattgtatta | gccttgagat | ttcaggtagt | attatcattg | 600 |
| agctgaaaga | tgcttataat | gcttgtacag | ataaagaaac | tattgaaaca | atattctata | 660 |
| ccgtgccaat | tgcagatata | tacagatccg | agcttgccca | taaccattcc | tttcatttag | 720 |
| atggagaaac | tgtaatattt | acagggaaag | gtacgtttaa | aggcttaata | tgttctaata | 780 |
| tatttgttga | aggggaaaga | ttcgattctc | aaacggggga | atgtttgggg | aaatatgtga | 840 |
| tcccattaag | tatagaaaag | aaaaataatg | tagattgtat | ctctatattt | ttaaattcag | 900 |
| aaaaaggtgg | gatttaacat | gatagtagat | ttatatagat | atttaggtgg | attggcagca | 960 |

-continued

```
gtaaatgccg tacttcactt gatttaaaca tgatagtaga tttatataga tatttaggtg    1020
gattggcagc agtaaatgcc gtacttcact tttatgagcc acgccctgat atatgtagga    1080
atataagcga agaatataac cttatagtat ttggagaccg tataccaact tttagcatag    1140
atccttcgca aataaatatt aacaatttat ctgtggacac tccagtggat gaaataacta    1200
ttaataacgt gagaagtata caattaatat ctagtcgttt tgaaaataca ggatttgtcg    1260
atactgaaaa ttattttact cctgaattat ctagaacagt tgtaaatagc atatctacat    1320
cgactactac aggatataag tacactcaat cccttactgt ttcatccaaa ttctccttta    1380
atttcccagt tgcgggtgca gaaaataata tttcattttc agtaggtttt gaacaaaacc    1440
tttcaactac agaaactaaa acagaaagta cttcaacgct tatgcgtata cctccacaac    1500
cagtttccgt aagacccaga acagcaaaaa gggttgaaat atcgctcttt gaattggcaa    1560
tccctagaat acaaaacgaa atttccggat tgtaacagg tactcttcca acaatttcaa    1620
attcgcatat ttccgatctt tatgctgtat taacacggac tgatagccta tgccctaatt    1680
catatattaa ccgagatgac ttttttaagaa tagatcatga aaataggggt ttgggattac    1740
aaggcttcgg ttctctcact ggaaatttaa catcattaga ttttgcaatt agaactactg    1800
aatatgattt accttcaaat acaattataa atatagagaa cgaaataaaa agagcccata    1860
tactcacaca gtaattaata gaaatagacc gataatcggt cttccccctg tcaagtaggc    1920
ctagtgacag ggttcttgct gtggaccgca aggtagcaaa tttctgaaga cccatatggg    1980
gtaccgtcag gaaaatgcgg atttacaacg ctaagcccat tttcctgacg attccccat    2040 ttttaacaac gttaagaaag tttcaatggt cttaaagaat ctaatgagat cattttctcc    2100
g                                                                     2101
```

<210> SEQ ID NO 42
<211> LENGTH: 310
<212> TYPE: PRT
<213> ORGANISM: Bacillus thuringiensis

<400> SEQUENCE: 42

```
Met Ala Ile Met Asn Pro Arg Pro Asp Ile Ala Gln Asp Ala Ala Arg
 1               5                  10                  15

Ala Trp Asp Ile Ile Ala Gly Pro Phe Ile Arg Pro Gly Thr Thr Pro
            20                  25                  30

Thr Asn Arg Gln Leu Phe Asn Tyr Gln Ile Gly Asn Ile Glu Val Glu
        35                  40                  45

Thr Pro Pro Gly Asn Leu Asn Phe Ser Val Val Pro Glu Leu Asp Phe
    50                  55                  60

Ser Val Ser Gln Asp Leu Phe Asn Asn Thr Ser Val Gln Gln Ser Gln
65                  70                  75                  80

Thr Tyr Ala Ser Phe Asn Glu Ser Arg Thr Val Val Glu Thr Thr Ser
                85                  90                  95

Thr Ala Val Thr His Gly Val Lys Ser Gly Val Thr Val Ser Ala Ser
            100                 105                 110

Ala Lys Phe Asn Ala Lys Ile Leu Val Lys Ser Ile Glu Gln Thr Ile
        115                 120                 125

Thr Thr Thr Val Ser Thr Glu Tyr Asn Phe Ser Ser Thr Thr Thr Arg
    130                 135                 140

Thr Asn Thr Val Thr Arg Gly Trp Ser Ile Pro Ala Gln Pro Val Leu
145                 150                 155                 160

Val Pro Pro His Ser Arg Val Thr Ala Thr Leu Gln Ile Tyr Lys Gly
```

-continued

```
                165                 170                 175
Asp Phe Thr Val Pro Val Leu Gln Asn Glu Leu Ser Leu Arg Val Tyr
                    180                 185                 190

Gly Gln Thr Gly Thr Leu Pro Ala Gly Asn Pro Ser Phe Pro Ser Asp
                195                 200                 205

Leu Tyr Ala Val Ala Thr Tyr Glu Asn Thr Leu Leu Gly Arg Ile Arg
    210                 215                 220

Glu His Ile Ala Pro Ala Leu Phe Arg Ala Ser Asn Ala Tyr Ile
225                 230                 235                 240

Ser Asn Gly Val Gln Ala Ile Trp Arg Gly Thr Ala Thr Arg Val
                    245                 250                 255

Ser Gln Gly Leu Tyr Ser Val Val Arg Ile Asp Glu Arg Pro Leu Ala
                260                 265                 270

Gly Tyr Ser Gly Glu Thr Arg Thr Glu Tyr Tyr Leu Pro Val Thr Leu
                275                 280                 285

Ser Asn Ser Ser Gln Ile Leu Thr Pro Gly Ser Leu Gly Ser Glu Ile
                290                 295                 300

Pro Ile Ile Asn Pro Val
305                 310

<210> SEQ ID NO 43
<211> LENGTH: 358
<212> TYPE: PRT
<213> ORGANISM: Bacillus thuringiensis

<400> SEQUENCE: 43

Trp Val Arg Tyr Asn Gln Phe Arg Arg Glu Leu Thr Leu Thr Val Leu
1                   5                   10                  15

Asp Ile Val Ala Leu Phe Ser Asn Tyr Asp Ser Arg Arg Tyr Pro Gly
                    20                  25                  30

Gly Ile Arg Thr Val Ser Gln Leu Thr Arg Glu Ile Tyr Thr Asn Pro
                35                  40                  45

Val Leu Cys Glu Asn Phe Ser Glu Asp Gly Ser Phe Arg Gly Met Ala
            50                  55                  60

Gln Arg Ile Glu Gln Asn Ile Arg Gln Pro His Leu Met Asp Ile Leu
65                  70                  75                  80

Asn Ser Ile Thr Ile Tyr Thr Asp Val His Arg Gly Phe Asn Tyr Trp
                    85                  90                  95

Ser Gly His Gln Ile Thr Ala Ser Pro Val Gly Phe Ser Gly Pro Glu
                100                 105                 110

Phe Ala Phe Pro Leu Phe Gly Asn Ala Gly Asn Ala Ala Pro Pro Val
            115                 120                 125

Leu Val Ser Leu Thr Gly Leu Gly Ile Phe Arg Thr Leu Ser Ser Pro
130                 135                 140

Leu Tyr Arg Tyr Thr Gln Arg Ile Ile Leu Gly Ser Gly Pro Asn Asn
145                 150                 155                 160

Gln Glu Leu Phe Val Leu Asp Gly Thr Glu Asn Asn Phe Ser Phe Ala
                165                 170                 175

Ser Leu Thr Thr Asn Leu Pro Ser Thr Ile Tyr Arg Gln Arg Gly Thr
                180                 185                 190

Val Asp Ser Leu Asp Val Ile Pro Pro Gln Asp Asn Ser Val Pro Pro
            195                 200                 205

Arg Ala Gly Lys Arg Val Glu Phe Ser Leu His Arg Leu Ser His Val
        210                 215                 220
```

Thr Met Leu Ser Gln Ala Ala Gly Ala Val Tyr Thr Leu Arg Ala Pro
225                 230                 235                 240

Thr Phe Ser Trp Gln His Arg Ser Ala Glu Phe Asn Asn Ile Ile Pro
            245                 250                 255

Ser Ser Gln Ser Leu Ile Thr Gln Ile Pro Leu Thr Lys Ser Thr Asn
                260                 265                 270

Leu Gly Ser Gly Thr Ser Val Val Lys Gly Pro Gly Phe Thr Gly Gly
            275                 280                 285

Asp Ile Leu Arg Arg Thr Ser Pro Gly Gln Ile Ser Thr Leu Arg Val
            290                 295                 300

Asn Ile Thr Ala Pro Leu Ser Gln Arg Tyr Arg Val Arg Ile Arg Tyr
305                 310                 315                 320

Ala Ser Thr Thr Asn Leu Gln Phe His Thr Ser Ile Asp Gly Arg Pro
                325                 330                 335

Ile Asn Gln Gly Asn Phe Ser Ala Thr Met Ser Ser Gly Ser Asn Leu
            340                 345                 350

Gln Ser Gly Ser Phe Arg
        355

<210> SEQ ID NO 44
<211> LENGTH: 980
<212> TYPE: DNA
<213> ORGANISM: Bacillus thuringiensis

<400> SEQUENCE: 44
attaaacact aaatacattc acattattct aacaaagaaa aggagtaata attatgaaac     60
atcataaaaa ttttgatcac atagtttggg acttcgctga aaagtggact gaacaaaagg    120
gggtagattt aaaaagggtc agttatgtag atcccattac tggtgaagat acattagagt    180
ttataaccaa atttaattat gttgggaaat tagaagaaaa agcttattgt ccagaagtaa    240
tagaaacaca atctttttca aactcaaatt gtgacgtttc gagggaattt ctaaagaaaa    300
aagtagacag gaaggaatgt tatttatggg atatagacta tgggtttatt ataccaactt    360
cggtacttac aaatccatta ttaccccca ctctcaatga aaaaattaat ccagcaatgg    420
aagtggactt atttaaaagt gcaaacctgt ttgaatccaa actaaataat tatagaatga    480
tagaagcagg tgtttatatt gaaccaaatc aagcagtaac cgccagcata atggttacac    540 caaacaagt acagcaagat tattgtatta gccttgagat ttcaggtagt attatcattg    600
agctgaaaga tgcttataat gcttgtacag ataaagaaac tattgaaaca atattctata    660
ccgtgccaat tgcagatata tacagatccg agcttgccca taaccattcc tttcatttag    720
atggagaaac tgtaatattt acagggaaag gtacgtttaa aggcttaata tgttctaata    780
tatttgttga agggggaaga ttcgattctc aaacgggga atgtttgggg aaatatgtga    840
tcccattaag tatagaaaag aaaaataatg tagattgtat ctctatattt ttaaattcag    900
aaaaaggtgg gatttaacat gatagtagat ttatatagat atttaggtgg attggcagca    960
gtaaatgccg tacttcactt                                               980

<210> SEQ ID NO 45
<211> LENGTH: 1121
<212> TYPE: DNA
<213> ORGANISM: Bacillus thuringiensis

<400> SEQUENCE: 45

-continued

```
gatttaaaca tgatagtaga tttatataga tatttaggtg gattggcagc agtaaatgcc      60
gtacttcact tttatgagcc acgccctgat atatgtagga atataagcga agaatataac     120
cttatagtat ttggagaccg tataccaact tttagcatag atccttcgca aataaatatt     180
aacaatttat ctgtggacac tccagtggat gaaataacta ttaataacgt gagaagtata     240
caattaatat ctagtcgttt tgaaaataca ggatttgtcg atactgaaaa ttattttact     300
cctgaattat ctagaacagt tgtaaatagc atatctacat cgactactac aggatataag     360
tacactcaat cccttactgt ttcatccaaa ttctccttta atttcccagt tgcgggtgca     420
gaaaataata tttcattttc agtaggtttt gaacaaaacc tttcaactac agaaactaaa     480
acagaaagta cttcaacgct tatgcgtata cctccacaac cagtttccgt aagacccaga     540
acagcaaaaa gggttgaaat atcgctcttt gaattggcaa tccctagaat acaaaacgaa     600
atttccggat ttgtaacagg tactcttcca acaatttcaa attcgcatat ttccgatctt     660
tatgctgtat taacacggac tgatagccta tgccctaatt catatattaa ccgagatgac     720
tttttaagaa aaatagggt ttgggattac ttgggattac aaggcttcgg ttctctcact     780
ggaaatttaa catcattaga ttttgcaatt agaactactg aatatgattt accttcaaat     840
acaattataa atatagagaa cgaaataaaa agagcccata tactcacaca gtaattaata     900
gaaatagacc gataatcggt cttccccctg tcaagtaggc ctagtgacag ggttcttgct     960
gtggaccgca aggtagcaaa tttctgaaga cccatatggg gtaccgtcag gaaaatgcgg    1020
atttacaacg ctaagcccat tttcctgacg attcccccat ttttaacaac gttaagaaag    1080
tttcaatggt cttaaagaat ctaatgagat cattttctcc g                        1121
```